US010363282B2

(12) United States Patent
Sanderson et al.

(10) Patent No.: US 10,363,282 B2
(45) Date of Patent: *Jul. 30, 2019

(54) ANALOGS OF C5A AND METHODS OF USING SAME

(71) Applicants: Board of Regents of The University of Nebraska, Lincoln, NE (US); San Diego State University Research Foundation, San Diego, CA (US)

(72) Inventors: Sam D. Sanderson, Omaha, NE (US); Joy Arlene Phillips, San Diego, CA (US); Edward Leroy Morgan, San Diego, CA (US); Marilyn Louise Thoman, San Diego, CA (US); Tamsin Sheen, San Diego, CA (US); Kelly S. Doran, San Diego, CA (US); Elizabeth Louise Virts, Carlsbad, CA (US); Tammy Kielian, Omaha, NE (US); Mark Hanke, Seattle, WA (US)

(73) Assignees: Board of Regents of The University of Nebraska, Lincoln, NE (US); San Diego State University Research Foundation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/869,396

(22) Filed: Jan. 12, 2018

(65) Prior Publication Data

US 2018/0140659 A1 May 24, 2018

Related U.S. Application Data

(62) Division of application No. 13/806,250, filed as application No. PCT/US2011/042344 on Jun. 29, 2011, now Pat. No. 9,895,411.

(60) Provisional application No. 61/359,444, filed on Jun. 29, 2010.

(51) Int. Cl.
*A61K 38/08* (2019.01)
*A61K 38/10* (2006.01)
*A61K 45/06* (2006.01)

(52) U.S. Cl.
CPC .............. *A61K 38/08* (2013.01); *A61K 38/10* (2013.01); *A61K 45/06* (2013.01); *Y02A 50/463* (2018.01); *Y02A 50/473* (2018.01)

(58) Field of Classification Search
None
See application file for complete search history.

(56) References Cited

U.S. PATENT DOCUMENTS

| 6,465,614 | B1 * | 10/2002 | Sanderson | ........... | C07K 14/472 |
| | | | | | 424/185.1 |
| 9,895,411 | B2 * | 2/2018 | Sanderson | ............. | A61K 38/10 |

| 2006/0148708 | A1 | 7/2006 | Li et al. |
| 2006/0160726 | A1 | 7/2006 | Fairlie et al. |
| 2008/0058252 | A1 | 3/2008 | Taylor et al. |

FOREIGN PATENT DOCUMENTS

WO  92/12168  7/1992

OTHER PUBLICATIONS

International Search Report in corresponding PCT Application Serial No. PCT/US2011/042344, dated Feb. 14, 2012.
Office Action in corresponding U.S. Appl. No. 13/806,250, dated Dec. 21, 2015.
Loeser, "Molecular Mechanisms of Cartilage Destruction: Mechanics, Inflammatory Mediators, and Aging Collide", Arthritis Rheum., May 2006, vol. 54, issue 5, pp. 1357-1360.
Gunther, et al., "Host defence against *Staphylococcus aureus* biofilms infection: phagocytosis of biofilms by polymorphonuclear neutrophils (PMN)", Mol Immunol., May 2009, vol. 46, issues 8-9, pp. 1805-1813.
Moline, et al., "Role of Neutrophil Leukocytes in Cutaneous Infection Caused by *Staphylococcus aureus*", Infect Immun., Nov. 2000, vol. 68, issue 11, pp. 6162-6167.
Office Action in corresponding U.S. Appl. No. 13/806,250, dated Jul. 20, 2016.
Casadevall, et al., Washington, D.C.: National Academies Press (US), 2006.
Office Action in corresponding U.S. Appl. No. 13/806,250, dated Jan. 5, 2017.
Hersh, et al., "Unmet Medical Need in Infectious Diseases", Correspondence, Jun. 2012, vol. 54, pp. 1677-1678.
CIDRAP News, Nov. 18, 2003, downloaded online on Dec. 12, 2016 from URL:<http:cidrap.umn.edu/news-perspective/2003/11/nih-launches-first-human-trial-ebola-vaccine>.
Mullin, "Ebola outbreak rages on as drug development remains slow", FierceBiotech, Jul. 11, 2014, downloaded online on Dec. 12, 2016 from URL:<http://www.fiercebiotech.com/r-d/ebola/outbreak-rages-on-as-drug-development-remains-slow>.
Aspergillosis, downloaded online on Dec. 12, 2016 from URL:<http://patient.info/doctor/aspergillosis>.
Franklin, et al., "You could have it and not even know it: An untreatable disease relating to cats" KFOR.com, Nov. 11, 2014, downloaded online on Dec. 12, 2016 from URL:<http://kfor.com/2014/11/11/you-could-have-it-and-not-even-know-it-An-untreatable-disease-relating-to-cats/>.
Goering, "Beware Beetle Kiss of Death", Chicago Tribune, Jan. 28, 1995, downloaded online on Dec. 12, 2016 from URL:<http://articles.chicagotribune.com/1995-01-28/news/9502020004_1_chagas-beetle-latin-america>.
Prion Alliance, "What are the potential treatments for prion disease?", Feb. 4, 2014, downloaded online on Dec. 12, 2016 from URL:<http://www.prionalliance.org/2014/02/04/what-are-the-potential-treatments-for-prion-disease/>.

(Continued)

*Primary Examiner* — Sergio Coffa
(74) *Attorney, Agent, or Firm* — Hovey Williams LLP

(57) ABSTRACT

Materials and methods for treating an infection or disease, activating an immune cell at a site of infection or disease, and for directly killing microorganisms, using response-selective carboxy-terminal C5a analogs, are provided.

9 Claims, No Drawings

Specification includes a Sequence Listing.

(56) References Cited

OTHER PUBLICATIONS

Walpole, et al., "The weight of nations: an estimation of adult human biomass", BMC Public Health, 2012, vol. 12, issue 439.
Cogen, et al., "Skin microbiota: a source of disease or defence?", Br J Dermatol., Mar. 2008, vol. 158, issue 3, pp. 442-455.
Postma, et al., "Chemotaxis inhibitory protein of *Staphylococcus aureus* binds specifically to the C5a and formylated peptide receptor", J Immunol . . . Jun. 1, 2004, vol. 172, issue 11, pp. 6994-7001.
Office Action in corresponding U.S. Appl. No. 13/806,250, dated Jun. 8, 2017.

* cited by examiner

SEQUENCE LISTING

```
<160> NUMBER OF SEQ ID NOS: 18

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45
```

```
Lys Ala Phe Thr Glu Cys Cys Val Val Ala Ser Gln Leu Arg Ala Asn
     50                  55                  60

Ile Ser His Lys Asp Met Gln Leu Gly Arg
 65                  70

<210> SEQ ID NO 2
<211> LENGTH: 10
<212> TYPE: PRT
<213> ORGANISM: Homo sapiens

<400> SEQUENCE: 2

Ile Ser His Lys Asp Met Gln Leu Gly Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (9)..(9)
<223> OTHER INFORMATION: D-Ala

<400> SEQUENCE: 3

Tyr Ser Phe Lys Pro Met Pro Leu Ala Arg
1               5                   10

<210> SEQ ID NO 4
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: N-methyl Leu
<220> FEATURE:
<221> NAME/KEY: MOD_RES
<222> LOCATION: (9)..(9)
<223> OTHER INFORMATION: D-Ala

<400> SEQUENCE: 4

Tyr Ser Phe Lys Asp Met Pro Leu Ala Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-methyl Leu
<220> FEATURE:
<221> NAME/KEY: MOD_RES
<222> LOCATION: (7)..(7)
<223> OTHER INFORMATION: D-Ala

<400> SEQUENCE: 5

Leu Arg Met Tyr Lys Pro Ala Phe Asp Ser
1               5                   10

<210> SEQ ID NO 6
<211> LENGTH: 10
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa is Tyr, Trp, or a N-acetyl derivatives of
      Tyr or Trp
<220> FEATURE:
<221> NAME/KEY: MOD_RES
<222> LOCATION: (5)..(5)
<223> OTHER INFORMATION: Xaa is Asp, Gly, Pro or a N-methyl derivatives
      of Asp or Gly
<220> FEATURE:
<221> NAME/KEY: MOD_RES
<222> LOCATION: (6)..(6)
<223> OTHER INFORMATION: Xaa is Ala, Cys, Leu, Met or a N-methyl
      derivatives of Ala, Cys, Leu or Met
<220> FEATURE:
<221> NAME/KEY: MOD_RES
<222> LOCATION: (7)..(7)
<223> OTHER INFORMATION: Xaa is Gln, Leu, Pro or a N-methyl derivatives
      of Gln or Leu
<220> FEATURE:
<221> NAME/KEY: MOD_RES
<222> LOCATION: (8)..(8)
<223> OTHER INFORMATION: Xaa is Pro, Leu, alpha-methyl Leu or N-methyl
      Leu
<220> FEATURE:
<221> NAME/KEY: MOD_RES
<222> LOCATION: (9)..(9)
<223> OTHER INFORMATION: Xaa is D-Ala, Gly, D-Pro, Aib or a N-methyl
      derivatives of D-Ala or Gly
<220> FEATURE:
<221> NAME/KEY: MOD_RES
<222> LOCATION: (10)..(10)
<223> OTHER INFORMATION: Xaa is Arg or N-methyl Arg

<400> SEQUENCE: 6

Xaa Ser Phe Lys Xaa Xaa Xaa Xaa Xaa Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 7

Tyr Ser Phe Lys Asp Ala Pro Leu Ala Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 8

Tyr Ser Phe Lys Asp Met Pro Leu Ala Arg
1               5                   10

<210> SEQ ID NO 9
```

```
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Tyr Ser Phe Lys Asp Met Pro Leu Gly Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Tyr Ser Phe Lys Asp Ala Pro Leu Gly Arg
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Tyr Ser Phe Lys Asp Cys Pro Leu Gly Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Pro

<400> SEQUENCE: 12

Tyr Ser Phe Lys Asp Met Pro Leu Pro Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: D-Ala

<400> SEQUENCE: 13

Tyr Ser Phe Lys Asp Met Gln Leu Ala Arg
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 14

Tyr Ser Phe Lys Asp Met Gln Leu Gly Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Tyr Ser Phe Lys Asp Met Gln Pro Gly Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Xaa is Aib

<400> SEQUENCE: 16

Tyr Ser Phe Lys Asp Met Pro Leu Xaa Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Tyr Ser Phe Lys Gly Met Pro Leu Gly Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Tyr Ser Phe Lys Gly Leu Leu Leu Gly Arg
1               5                   10
```

ANALOGS OF C5A AND METHODS OF USING SAME

CROSS-REFERENCE TO RELATED APPLICATIONS

This application is a divisional of U.S. Ser. No. 13/806,250, filed Sep. 25, 2013, which is the U.S. National Stage of International Application No. PCT/US2011/042344, filed Jun. 29, 2011, which claims benefit to U.S. Provisional Application Ser. No. 61/359,444, filed Jun. 29, 2010, each of which is incorporated herein by reference in its entirety.

STATEMENT REGARDING FEDERALLY-SPONSORED RESEARCH OR DEVELOPMENT

This invention was made with U.S. government support under grant numbers RO1 GM095884, RO1 AG028077, AI 065712, and P01 AI083211 awarded by the National Institutes of Health. The government has certain rights in the invention.

SEQUENCE LISTING

This applicant contains, as a separate part of disclosure, a Sequence Listing in computer-readable form (filename: Sequence_Listing.txt, created Jun. 27, 2011; 5,610 bytes—ASCII text file) which is incorporated by reference in its entirety.

FIELD OF THE INVENTION

The present disclosure relates to materials and methods for treating and preventing an infection or disease, and for directly killing microorganisms. More specifically, the present disclosure relates to the use of carboxy-terminal (C-terminal) C5a analogs for treating and preventing an infection or disease, and for directly killing microorganisms.

BACKGROUND OF THE INVENTION

The blood complement (C) plays an important role in host defense to foreign substances. Individuals that are deficient in certain C components often suffer recurrent and sometimes fatal infections. Activation of the C system results in the production of the anaphylatoxins, C3a and C5a. These fragments are biologically active cleavage products of the larger C proteins C3 and C5, respectively. C5a is a short (74 residues in human) glycoprotein that is generated by enzymatic cleavage of C5.

C5a is recognized as a principal mediator of local and systemic inflammatory responses because of its ability to activate and recruit neutrophils, induce spasmogenesis, increase vascular permeability and stimulate the release of secondary inflammatory mediators from a variety of cell types (e.g., leukocytes and macrophages). C5a also appears to play a role in the modulation of immune response because of its ability to induce, directly or indirectly, the synthesis and release of the cytokines interleukin-1 (IL-1), interleuken-6 (IL-6), interleukin-8 (IL-8), and tumor necrosis factor-α (TNF-α) from human monocytes. These inflammatory and immunomodulatory activities are believed to be expressed via a transmembrane, G-protein-mediated signal transduction mechanism when the C5a ligand interacts with its receptor(s) expressed on the surface of certain circulating and tissue cell types.

The proinflammatory activities of C5a may be classified into two broad categories. The first category of activity is generally associated with the release of histamines and other secondary mediators (e.g., vasoconstrictor and vasodilator eicosanoids). These activities of C5a affect many systems, and are associated with the phenomena of spasmogenesis and certain cell aggregatory activities (e.g., platelet aggregation). The second category of activity involves recruitment and activation of neutrophils and subsequent effects of such neutrophil accumulation and activation, such as increased vascular permeability, release of cytokines and other pro-inflammatory responses. The in vivo pharmacology of these two broad classes of C5a activities is described briefly by Drapeau et al. (1993), Biochem. Pharmacol., 45: 1289-1299. The regulation of neutrophils and other leukocytes by C5a has been reviewed by Hugh & Morgan (1984), Chapter 4 in Regulation of Leukocyte Function, R. Snyderman, ed., Plenum Publishing Corp., pp. 109-153.

Because of its proinflammatory activity, C5a has been implicated as a pathogenic factor in the expression of certain inflammatory disorders, such as rheumatoid arthritis, adult respiratory distress syndrome, gingivitis, and the tissue damage associated with atherosclerosis and myocardial infarction. Consequently, considerable research efforts have been expended in developing specific C5a antagonists for use as anti-inflammatory agents in the treatment of these diseases.

C-terminal C5a peptide analogs have been produced and studied for the purpose of developing C5a agonists and antagonists. For example, Ember et al. (Ember et al. (1992), J. Immunol., 148: 3165-3173) characterized the biological activities of 22 synthetic C-terminal C5a analogs. The analogs were reported to be full agonists of natural C5a, having in vitro activities characteristic of naturally occurring C5a, including the ability to stimulate ileal contraction (i.e., spasmogenesis) platelet aggregatory activation and neutrophil polarization and chemotaxis. However, the potencies of even the most effective of these analogs was on the order of only 0.01-0.25% that of the natural factor. This level of potency could be obtained with analogs as short as decapeptides, as compared with longer C-terminal peptides that had previously been studied as potential agonists. Morgan et al. (1992), J. Immunol., 148: 3937-3942, reported that certain of the peptide analogs disclosed by Ember et al. stimulated synthesis of interleukin-6 in human peripheral blood mononuclear cells. Again, however, potency of these peptide analogs was on the order of 0.01-0.1% of either natural or recombinant C5a. Drapeau et al. (supra) reported on the pharmacology, metabolism and in vivo cardiovascular and hematologic effects of synthetic C-terminal C5a peptide analogs based on either human or porcine amino acid sequences. These analogs were also found to be agonists of natural C5a, but were disclosed as being at least 1,000-fold less potent than recombinant C5a as measured by competition for C5a binding sites.

C-terminal C5a peptide analogs have also been studied with respect to the ability of such analogs to bind to C5a receptors. Kawai et al. (1992), J. Med. Chem., 35: 220-223, reported on relationships between the hydrophobicity and chirality of residues 70-73 of C-terminal octapeptide analogs and the ability of such analogs to bind to C5a receptors. However, biological responses elicited by these octapeptide analogs was not reported. In other studies, it has been determined that substitution of phenylalanine or tryptophan in positions between 65 and 69 of the human C5a C-terminus could enhance or decrease potency, depending on whether the substitution was made at position 67 or at position 66 (Or et al. (1992) J. Med. Chem. 35: 402-406; Mollison et al. (1991) Agents Actions Suppl. 35:17-21; Siciliano et al. (1994) Proc. Natl. Acad. Sci USA 91:1214-1218). In other studies, these observations were corroborated with reports that substitution of phenylalanine for histidine at position 67 substantially increased the potency of a number of C-terminal peptide analogs of human C5a (Mollison et al. (1991), Agents and Actions, Suppl. 35: 17-21; Or et al. J. Med. Chem., (1992), 35: 402-406; and Kohl et al. (1993), Eur. J. Immunol., 23: 646-652). These reports did not address any differences among the various peptide analogs with respect to their effectiveness for eliciting specific biological responses associated with C5a.

U.S. Pat. No. 5,696,230, which is incorporated by reference in its entirety, describes a conformational characterization of C-terminal peptide analogs of human C5a. U.S. Pat. No. 6,821,517, also incorporated by reference in its entirety, describes compositions and methods for delivering specific antigens to antigen-presenting cells (APCs). Several research articles have published that similarly describe the use of a C-terminal analog of C5a conjugated to a specific antigen (Tempero et al. (1996) J. Immunol. 158:1377-1382; Buchner et al. (1996) J. Immunol. 158:1670-1680; Ulrich et al. (2000) J. Immunol. 164:5492-5498; Sanderson et al. (2003) Int. Immunopharmacol. 3:137-146; Floreani et al. (2007) Cell Cycle 6:2835-2839; Hegde et al. (2008) Int. Immunopharmacol. 8:819-827; Duryee et al. (2009) Vaccine 27:2981-2988; Morgan et al., Vaccine, 28(2): 463-469 (2009); Morgan et al. (2010) Vaccine 28:8275-8279).

To date, the use of oligopeptide C-terminal analogs of C5a, that are not conjugated to a specific antigen, have not been shown to demonstrate therapeutic properties for treating infections and diseases.

Thus, a need exists to develop therapeutic molecules useful for the treatment of infections and diseases, including infections caused by antibiotic resistant bacteria and bacterial burdens due to biofilms.

SUMMARY OF THE INVENTION

The present disclosure fulfills the aforementioned need in the art by providing materials and methods for treating and/or preventing infections or diseases using an oligopeptide C-terminal analog of C5a. For example, selective activation of host innate immunity, which would not only induce the body's inherent first line of defense to infections but would contribute few mutational pressures since the therapeutic effect is neither directed to nor imposed upon the bacteria, is contemplated by the present disclosure. In various embodiments, selective activation of host immunity is useful for fighting infections and various diseases, in general.

In one embodiment of the present disclosure, a method of treating an infection or disease is provided comprising administering an effective amount of an oligopeptide carboxy-terminal (C-terminal) analog of C5a to a mammal, said analog not attached to an antigen, and said analog having C5a receptor binding activity.

In another embodiment, the disclosure provides a method of preventing an infection or disease comprising administering an effective amount of an oligopeptide C-terminal analog of C5a to a mammal, said analog not attached to an antigen, and said analog having C5a receptor binding activity.

In another embodiment, a method of activating an immune cell at a site of infection or disease is provided comprising administering an effective amount of an oligopeptide C-terminal analog of C5a to a mammal, said analog not attached to an antigen, and said analog having C5a receptor binding activity.

In various aspects of each embodiment of the method, the analog is 10 amino acid residues in length. In certain aspects of each embodiment of the method, the analog comprises the formula: A1-Ser-Phe-Lys-A2-A3-A4-A5-A6-A7 (SEQ ID NO: 6), wherein: A1 is Tyr, Trp, or N-acetyl derivatives of Tyr or Trp; A2 is Asp, Gly, Pro or N-methyl derivatives of Asp or Gly; A3 is Ala, Cys, Leu, Met or N-methyl derivatives of Ala, Cys, Leu or Met; A4 is Gln, Leu, Pro or N-methyl derivatives of Gln or Leu; A5 is Pro, Leu, α-methyl Leu or N-methyl Leu; A6 is D-Ala, Gly, D-Pro, Aib aminoisobutyric acid (Aib)] or N-methyl derivatives of D-Ala or Gly; and A7 is Arg or N-methyl Arg.

In still other aspects of each embodiment of the method, the analog is selected from the group consisting of: (a) Tyr-Ser-Phe-Lys-Asp-Met-Pro-MeL-(D-Ala)-Arg (SEQ ID NO: 4); [MeL is N-methyl Leu]; (b) Tyr-Ser-Phe-Lys-Pro-Met-Pro-Leu-(D-Ala)-Arg (SEQ ID NO: 3); (c) Tyr-Ser-Phe-Lys-Asp-Ala-Pro-Leu-(D-Ala)-Arg (SEQ ID NO: 7); (d) Tyr-Ser-Phe-Lys-Asp-Met-Pro-Leu-(D-Ala)-Arg (SEQ ID NO: 8); (e) Tyr-Ser-Phe-Lys-Asp-Met-Pro-Leu-Gly-Arg (SEQ ID NO: 9); (f) Tyr-Ser-Phe-Lys-Asp-Ala-Pro-Leu-Gly-Arg (SEQ ID NO: 10); (g) Tyr-Ser-Phe-Lys-Asp-Cys-Pro-Leu-Gly-Arg (SEQ ID NO: 11); (h) Tyr-Ser-Phe-Lys-Asp-Met-Pro-Leu-(D-Pro)-Arg (SEQ ID NO: 12); (i) Tyr-Ser-Phe-Lys-Asp-Met-Gln-Leu-(D-Ala)-Arg (SEQ ID NO: 13); (j) Tyr-Ser-Phe-Lys-Asp-Met-Gln-Leu-Gly-Arg (SEQ ID NO: 14); (k) Tyr-Ser-Phe-Lys-Asp-Met-Gln-Pro-Gly-Arg (SEQ ID NO: 15); (l) Tyr-Ser-Phe-Lys-Asp-Met-Pro-Leu-Aib-Arg (SEQ ID NO: 16); (m) Tyr-Ser-Phe-Lys-Gly-Met-Pro-Leu-Gly-Arg (SEQ ID NO: 17); and (n) Tyr-Ser-Phe-Lys-Gly-Leu-Leu-Leu-Gly-Arg (SEQ ID NO: 18).

In still another aspect of each embodiment of the method, the analog is Tyr-Ser-Phe-Lys-Asp-Met-Pro-MeL-(D-Ala)-Arg (SEQ ID NO: 4) or the analog is: Tyr-Ser-Phe-Lys-Pro-Met-Pro-Leu-(D-Ala)-Arg (SEQ ID NO: 3).

In various aspects of each embodiment of the disclosure, the infection or disease is caused by an infectious agent selected from the group consisting of bacteria, virus, fungus, parasite, protozoan, and prion. In other various aspects of each embodiment, the disease is cancer. In various aspects of each embodiment of the method, the infection comprises a biofilm.

In various aspects of each embodiment of the disclosure involving a bacterial infection, the bacteria is selected from the group consisting of methicillin-resistant *S. aureus* (MRSA), MRSA strain USA300-FPR3757, vancomycin-resistant *S. aureus* (VRSA), macrolide-resistant *S. pyogenes*, penicillin-resistant *Streptococcus pneumoniae*, Extensively Drug-Resistant *Mycobacterium tuberculosis* (XDR TB), multidrug-resistant *Enterococcus faecalis*, multidrug-resistant *Enterococcus faecium*, *Pseudomonas aeruginosa*, clindamycin-resistant *Clostridium difficile*, fluoroquinolone-resistant *Clostridium difficile*, *Acinetobacter baumannii*, *Bacillus anthraces*, *Bordetella pertussis*, *Borrelia burgdorferi*, *Brucella abortus*, *Brucella canis*, *Brucella melitensis*, *Brucella suis*, *Campylobacter jejuni*, *Chlamydia pneumonia*, *Chlamydia trachomatis*, *Chlamydophila psittaci*, *Clostridium botulinum*, *Clostridium difficile*, *Clostridium perfringens*, *Clostridium tetani*, *Corynebacterium diphtheriae*, *Enterococcus faecalis*, *Enterococcus faecium*, *Escherichia coli*, *Francisella tularensis*, *Haemophilus influenzae*, *Helicobacter pylori*, *Legionella pneumophila*, *Leptospira interrogans*, *Listeria monocytogenes*, *Mycobacterium leprae*, *Mycobacterium tuberculosis*, *Mycobacterium ulcerans*,

*Mycoplasma pneumoniae, Neisseria gonorrhoeae, Neisseria meningitidis, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus mutans, Streptococcus pneumoniae, Streptococcus pyogenes, Treponema pallidum, Vibrio cholerae,* and *Yersinia pestis.*

In various aspects of each embodiment of the disclosure involving a viral infection, the virus is selected from the group consisting of Poxviridae, Chordopoxvirinae, Orthopoxvirus, Cowpoxvirus, Monkeypox virus, Vaccinia virus, Variola virus, Parapoxvirus, Bovine papular stomatitis virus, Orf virus, Pseudocowpox virus, Molluscipoxvirus, Molluscum contagiosum virus, Yatapoxvirus, Tanapox virus, Yaba monkey tumor virus, Herpesviridae, Alphaherpesvirinae, Simplexvirus, Human herpesvirus 1, Herpes simplex virus 1, Human herpesvirus 2, Herpes simplex virus 2, Varicellovirus, Human herpesvirus 3, Varicella-zoster virus, Betaherpesvirinae, Cytomegalovirus, Human herpesvirus 5, Human cytomegalovirus, Roseolovirus, Human herpesvirus 6, Human herpesvirus 7, Gammaherpesvirinae, Lymphocryptovirus, Human herpesvirus 4, Epstein-Barr virus, Rhadinovirus, Human herpesvirus 8, Kaposi's sarcoma-associated herpesvirus, Adenoviridae, Mastadenovirus, Human adenovirus A, Human adenovirus B, Human adenovirus C, Human adenovirus D, Human adenovirus E, Human adenovirus F, Polyomaomaviridae, Polyomavirus, BK polyomavirus, Human polyomavirus, JC polyomavirus, Papillomaviridae, Alphapapillomavirus, Human papillomavirus 2, Human papillomavirus 10, Human papillomavirus 6, Human papillomavirus 7, Human papillomavirus 16, Human papillomavirus 18, Human papillomavirus 26, Human papillomavirus 32, Human papillomavirus 34, Human papillomavirus 53, Human papillomavirus 54, Human papillomavirus 61, Human papillomavirus 71, Human papillomavirus cand90, Betapapillomavirus, Human papillomavirus 5, Human papillomavirus 9, Human papillomavirus 49, Human papillomavirus cand92, Human papillomavirus cand96, Gammapapillomavirus, Human papillomavirus 4, Human papillomavirus 48, Human papillomavirus 50, Human papillomavirus 60, Human papillomavirus 88, Mupapillomavirus, Human papillomavirus 1, Human papillomavirus 63, Parvoviridae, Parvovirinae, Erythrovirus, B19 virus, Hepadnaviridae, Orthohepadnavirus, Hepatitis B virus, Retroviridae, Orthoretrovirinae, Deltaretrovirus, Primate T-lymphotropic virus 1, Primate T-lymphotropic virus 2, Lentivirus, Human immunodeficiency virus 1, Human immunodeficiency virus 2, Reoviridae, Orthoreovirus, Mammalian orthoreovirus, Orbivirus, African horse sickness virus, Changuinola virus, Corriparta virus, Orungo virus, Rotavirus, Rotavirus A, Rotavirus B, Mononegavirales, Filoviridae, Marburgvirus, Lake Victoria marburgvirus, Ebolvirus, Ivory Coast ebolavirus, Reston ebolavirus, Sudan ebolavirus, Zaire ebolavirus, Paramyxoviridae, Paramyxovirinae, Respirovirus, Human parainfluenza virus 1, Human parainfluenza virus 3, Morbillivirus, Measles virus, Edmonston virus, Rubulavirus, Human parainfluenza virus 2, Human parainfluenza virus 4, Mumps virus, Henipavirus, Hendravirus, Nipahvirus, Pneumovirinae, Pneumovirus, Human respiratory syncytial virus, Metapneumovirus, Human metapneumovirus, Rhabdoviridae, Vesiculovirus, Chandipura virus, Cocal virus, Isfahan virus, Piry virus, Vesicular stomatitis Alagoas virus, Vesicular stomatitis Indiana virus, Vesicular stomatitis New Jersey virus, Lyssavirus, Australian bat lyssavirus, Rabies virus, Orthomyxoviridae, Influenzavirus A, Influenza A virus, Influenzavirus B, Influenza B virus, Influenzavirus C, Influenza C virus, Bunyaviridae, Bunyavirus, Bunyamwera virus, Bwamba virus, California encephalitis virus, Guama virus, Oriboca virus, Oropouche virus, Hantavirus, Andes virus, Hantaan virus, Puumala virus, Seoul virus, Dobrava-Belgrade virus, Bayou virus, Black Creek Canal virus, New York virus, Sin Nombre virus, Nairovirus, Crimean-Congo hemorrhagic fever virus, Nairobi sheep disease virus, Phlebovirus, Rift Valley fever virus, Sandfly fever Naples virus, Arenaviridae, Arenavirus, Lassa virus, Lymphocytic choriomeningitis virus, Guanarito virus, Junín virus, Machupo virus, Sabiávirus, Deltavirus, Hepatitis delta virus, Nidovirales, Coronaviridae, Coronavirus, Human coronavirus 229E, Human coronavirus OC43, Human enteric coronavirus, Severe acute respiratory syndrom coronavirus, Torovirus, Picornaviridae, Enterovirus, Human enterovirus A, Human enterovirus B, Human enterovirus C, Human enterovirus D, Poliovirus, Rhinovirus, Human rhinovirus A, Human rhinovirus B, Hepatovirus, Hepatitis A virus, Parechovirus, Human parechovirus, Caliciviridae, Norovirus, Norwalk virus, Sapovirus, Sapporo virus, Hepevirus, Hepatitis E virus, Astroviridae, Mamastrovirus, Human astrovirus, Togaviridae, Alphavirus, Chikungunya virus, O'nyong-nyong virus, Mayaro virus, Ross River virus, Barmah Forest virus, Sindbis virus, Ockelbo virus, Venezuelan equine encephalitis virus, Western equine encephalitis virus, Eastern equine encephalitis virus, Rubivirus, Rubella virus, Flaviviridae, Flavivirus, Kyasanur Forest disease virus, Omsk hemorrhagic fever virus, Powassan virus, Louping ill virus, Tick-borne encephalitis virus, Dengue virus, Japanese encephalitis virus, Murray Valley encephalitis virus, St. Louis encephalitis virus, West Nile virus, Ilheus virus, Yellow fever virus, Apoi virus, Hepacivirus, Hepatitis C virus, GB virus B, and GB virus A.

In various aspects of each embodiment involving a fungus, the fungus is selected from the group consisting of *C. albicans, A. fumigates, A. flavus, A. clavatus, C. neoformans, C. laurentii, C. albidus, C. gatti, H. capsulatum, P. jirovecii, S. chartarum, C. immitis* and *C. posadasii.*

In various aspects of each embodiment involving a parasite, the parasite is selected from the group consisting of protozoans, helminthes, parasitic worms, Halzoun syndrome, myiasis, Chogoe fly, human botfly, candiru, bedbug, head louse, body louse, crab louse, demodex, scabies, and screwworm.

In various aspects of each embodiment involving a protozoan, the protozoan is selected from the group consisting of *Entamoeba Histolytica, Giardia Lambda, Trichomonas Vaginalis, Trypanosoma Brucei, T. Cruzi, Leishmania Donovani, Balantidium Coli, Toxoplasma Gondii, Plasmodium* Spp., and *Babesia Microti.*

In various aspects of each embodiment of the disclosure, the disease is selected from the group consisting of scrapie, bovine spongiform encephalopathy, transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, and Kuru.

In various aspects of each embodiment of the method, the analog is administered by a route selected from the group consisting of oral, topical, inhalation spray, intradermal, subcutaneous injection, and intravenous injection.

In still other various aspect of each embodiment of the method, the analog is formulated in a powder, aerosol, cream, gel, liquid, bandage, and surgical suture.

In various aspects of each embodiment of the method, the analog is administered at a dose of 25 μg to 500 μg.

In various aspects of each embodiment of the disclosure, the analog is administered concurrently, prior, or following administration of a second therapeutic agent. The second therapeutic agent, in various aspects, is selected from the group consisting of vaccine, antibiotic, antifungal, and antiparasitic.

In various aspects of each embodiment of the method involving a vaccine, the vaccine is a C-terminal analog of C5a attached to an antigen.

In various aspects of each embodiment of the disclosure, the mammal is a human selected from the group consisting of: fetus, newborn, infant, child, young adult, adult, elder, and immunocompromised.

The disclosure further provides, in another embodiment, a method of treating an influenza infection comprising administering an effective amount of C5a analog EP67 to a mammal.

In another embodiment, the disclosure provides a method of treating a dermal S. aureus infection comprising administering an effective amount of C5a analog EP67 to a mammal.

In another embodiment, the disclosure provides a method of treating a Group B Streptococcus (GBS) infection comprising administering an effective amount of C5a analog EP67 to a mammal.

In another embodiment, the disclosure provides a method of killing a microbial cell comprising administering an effective amount of C5a analog EP67 to a microbial cell.

In another embodiment, the disclosure provides a method of treating a biofilm comprising administering an effective amount of C5a analog EP67 to a microbial cell.

DETAILED DESCRIPTION

As disclosed herein, a variety of diseases and/or infections can be treated and/or prevented by administering C-terminal analogs of C5a. In one embodiment of the present disclosure, airborne pathogens are treated and/or prevented by administering C-terminal analogs of C5a. Currently, no effective method exists for enhancing airway immune responsiveness to airborne pathogens. Typically, an enhanced immune response is approached by vaccination with a specific vaccine developed toward a single pathogen (such as seasonal influenza) and administered either by injection or by an intranasal mist. However, this approach is encumbered by the logistics and costs of developing and distributing an effective vaccine to pathogens that mutate from year to year.

In one embodiment, the present disclosure provides effective protection against airborne pathogens by the intranasal administration of a C-terminal analog of C5a (such as EP67 described herein). Unlike conventional vaccines, C-terminal analog of C5a can be generated economically and rapidly in huge quantities by standard solid-phase peptide synthesis, purified to 100% purity, and stored as a dry lyophilized powder which has a shelf life of years at room temperature. Moreover, in another embodiment, administration of C-terminal analogs of C5a has the advantage of inducing airway immune protection to any type of airborne pathogen, thus providing a level of protection allowing a window of time for the administration of pathogen-specific vaccines. As disclosed herein, C-terminal analogs of C5a not only heighten airway immunity prior to pathogen exposure, but can activate airway immunity and, consequently, decrease recovery time after pathogen exposure. In other words, C-terminal analogs of C5a induce both prophylactic and therapeutic mucosal (airway) immune responses.

In another embodiment of the present disclosure, the ability to complement C-terminal analogs of C5a -mediated therapy, for example, with existing antivirals (e.g., Tamiflu™), existing vaccines, and also C-terminal analogs of C5a-containing vaccines to influenza (e.g., EP67 conjugated to an influenza-derived antigen/epitope) is provided. Such C-terminal analogs of C5a-containing vaccines are generated by the covalent attachment of C-terminal analogs of C5a to the intact influenza virus, proteins from the interior and/or the surface of the virus, or epitopes derived from these proteins.

Given the ability of C-terminal analogs of C5a to induce general immune responsiveness, the administration of C-terminal analogs of C5a also heightens immunologic surveillance to other diseases such as cancer and, in similar fashion, provide a window of time to allow the administration of patient-specific vaccines, including C-terminal analogs of C5a-containing cancer vaccines.

In yet another embodiment of the present disclosure, bacterial infections are treated and/or prevented by administering C-terminal analogs of C5a. The prevalence of bacterial infections along with the emergence of antibiotic-resistant bacteria, such as methicillin-resistant S. aureus (MRSA) have complicated the treatment and control of these infections in the United States and Third World countries. The pace by which these bacteria can mutate and evade standard antibiotic treatment exceeds the pace of development of new antibiotics to fight them. The present disclosure provides materials and methods for the use of a C-terminal analog of C5a as a way of activating the innate arm of immunity to fight these bacterial infections. This is achieved by a simple subcutaneous injection or topical application (or, in various embodiments, administration by one or more means described below) of a C-terminal analog of C5a formulated in a cream to the infection site. As discussed herein, C-terminal analogs of C5a invoke localized and/or systemic innate immune responses that recruit/activate the necessary immune cells to the infection site such that it is eliminated/reduced. Considering the aforementioned ability to produce large, highly pure and stable quantities of C-terminal analogs of C5a, distribution to remote field clinics/hospitals and combat areas and its subsequence storage and stability once delivered to these areas is simple and requires no expensive storage facilities/equipment such as refrigerators.

In still another embodiment of the present disclosure, a C-terminal analog of C5a is used to treat, e.g., antibiotic-resistant bacteria or difficult-to-treat fungal and viral infections by directly interacting with the pathogen as described herein. Of course, in addition to this direct effect, C-terminal analogs of C5a invoke innate immunity against the bacteria as described herein and, consequently, affords a dual mechanism of action not realized by standard antibiotics or other antibacterial peptides.

In yet another embodiment, a C-terminal analog of C5a is used to therapeutically and/or prophylactically reduce bacterial burdens in biofilms associated with catheters and other artificial implants. Bacteria within a biofilm are not responsive to conventional antibiotic treatment since they are physically protected from access to the antibiotics by the biofilm matrix. More importantly, the bacteria within a biofilm have assumed a sessile state and are refractory to antibiotics, which typically target the cell wall and ribosomal components of active/growing bacteria. Likewise, bacteria are protected from the cellular and molecular components of host immunity making immunotherapy/vaccines problematic. Indeed, the various components of the biofilm matrix appear to have an immunosuppressive effect on the cellular components of immunity (particularly macrophages) in the vicinity of the biofilm. As a result, the only option for dealing with biofilms developing around an artificial device is a cycle of removal and replacement—an inconvenient, ineffective and undesirable process. These difficulties of biofilm treatment/control are underscored even further when it is associated with more permanent artificial implants such as hips, knees and heart valves. In addition, this issue becomes even more pronounced against the backdrop of the rapidly increasing population of the elderly who will be the primary recipients of such artificial implants and who grow increasingly less immunosuppressive with age.

Thus, in one embodiment, the use of a C-terminal analog of C5a overcomes the aforementioned issues of biofilm treatment and control. As described herein, C-terminal analogs of C5a provide the activation signals to C5a receptor-bearing macrophages (and other APCs) to mount a robust innate immune response to the bacteria in a biofilm and surrounding tissues. Treatment with a C-terminal analog of C5a is among the first such approaches to have shown a therapeutically viable method for controlling bacterial burden in a biofilm.

General Definitions

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a particular C-terminal analog of C5a is a reference to one such analog or a plurality of such analogs, including equivalents thereof. Also, the terms "at least one" and "one or more" have the same meaning and include one, two, three or more. The following terms, unless otherwise indicated, shall be understood to have the following meanings when used in the context of the present disclosure.

Examples provided herein, including those following "such as" and "e.g.," are considered as illustrative only of various aspects of the present disclosure and embodiments thereof, without being specifically limited thereto. Any suitable equivalents, alternatives, and modifications thereof (including materials, substances, constructions, compositions, formulations, means, methods, conditions, etc.) known and/or available to one skilled in the art may be used or carried out in place of or in combination with those disclosed herein, and are considered to fall within the scope of the present disclosure.

As used in the present disclosure, the term "treating" or "treatment" refers to an intervention performed with the intention of preventing the further development or altering the pathology of a disease or infection. Accordingly, "treatment" refers to both therapeutic treatment and prophylactic or preventative measures. "Preventing" refers to a preventative measure taken with a subject not previously exposed to or infected with a particular pathogen. A therapeutic agent may directly decrease the pathology of a disease or infection, or render the disease or infection more susceptible to treatment by other therapeutic agents or, for example, the host's immune system. Treatment of patients suffering from clinical, biochemical, radiological or subjective symptoms of a disease or infection may include alleviating some or all of such symptoms or reducing the predisposition to the disease. Improvement after treatment may be manifested as a decrease or elimination of such symptoms.

"Infections" as used herein refers to any microbial invasion of a living tissue that is deleterious to the organism (host). Microbial infections may be caused by microorganisms, or "infectious agents," including, but not limited to, a bacteria, virus, fungus, parasite, protozoan, prion. Similarly, the term "disease" refers to any pathological condition and includes the overt presentation of symptoms (i.e., illness) or the manifestation of abnormal clinical indicators (e.g., biochemical indicators). Alternatively, the term "disease" refers to a genetic or environmental risk of or propensity for developing such symptoms or abnormal clinical indicators. An infection or disease is any condition that would benefit from treatment with a molecule according to the present disclosure. This includes chronic and acute disorders or diseases including those pathological conditions which predispose the mammal to the disorder in question. In various embodiments of the invention, cancer cells (e.g., a cell that grows and/or divides at an unregulated, quickened pace) or other transformed cells (e.g., a cell that has been genetically changed by a virus to a tumor cell) are contemplated.

As used herein, the phrase "effective amount" or "therapeutically effective amount" is meant to refer to an amount of therapeutic or prophylactic C-terminal analog of C5a that would be appropriate for an embodiment of the present disclosure, that will elicit the desired therapeutic or prophylactic effect or response, including alleviating some or all of such symptoms of disease or infection or reducing the predisposition to the disease or infection, when administered in accordance with the desired treatment regimen.

The term "oligopeptide" refers to a peptide that is at least about 5 amino acids in length; for example at least 10 amino acids in length; for example at least about 20 amino acids in length; and at least about 50 amino acids in length. In one embodiment of the present disclosure, the oligopeptide is a decapeptide (i.e., 10 amino acids in length).

As used herein, the term "carboxy-terminal" or "C-terminal" refers to the carboxy-terminus of C5a.

As used herein "biologically active derivative," "biologically active fragment," "biologically active analog" or "biologically active variant" includes any derivative or fragment or analog or variant of a molecule having substantially the same functional and/or biological properties of said molecule, such as binding properties, and/or the same structural basis, such as a peptidic backbone or a basic polymeric unit.

An "analog," such as a "variant" or a "derivative," is a compound substantially similar in structure and having the same biological activity, albeit in certain instances to a differing degree, to a naturally-occurring molecule.

A "derivative," for example, is a type of analog and refers to a peptide or oligopeptide sharing the same or substantially similar structure as a reference polypeptide that has been modified, e.g., chemically.

As used herein, the phrase "not attached to an antigen" refers to a C-terminal analog of C5a that is not attached (linked or conjugated; e.g., via a peptide bond) to an antigen for the purpose of stimulating a specific immune response against that antigen. Of course, the phrase "attached to an antigen" refers to a C-terminal analog of C5a that is attached (linked or conjugated; e.g., via a peptide bond) to an antigen for the purpose of stimulating a specific immune response against that antigen.

As used herein, the phrase "having C5a receptor binding activity" refers to the ability of a C-terminal C5a analog to bind to CD88. According to the present disclosure, the binding of a C-terminal C5a analog to CD88 causes one or more biological activities or responses, including but not limited to, activation of antigen presenting cells (APCs).

As used herein, "concurrent" administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks. "Prior" administration refers to administering a C-terminal analog of C5a at some time before administering a second therapeutic agent, irrespective of whether the two therapeutic agents are exerting a therapeutic effect together. Moreover, "following" administration refers to administering a C-terminal analog of C5a at some time after administering a second therapeutic agent, irrespective of whether the two therapeutic agents are exerting a therapeutic effect together.

"Mammal" for purposes of treatment and prevention refers to any animal classified as a mammal, including humans, domestic and farm animals, and zoo, sports, or pet animals, such as dogs, horses, cats, cows, etc. In one embodiment, the mammal is human.

As used herein, the following terms refer to a mammal according to the following age ranges: fetus (about 9 weeks after fertilization to birth), newborn (birth to about 28 days, including premature, post mature and full term newborns), infant (about 1 month to about 12 months), child (about 1 year to about 13 years, including, e.g., toddlers, pre-teenagers and early teenagers), young adult (from about 13 years to 18 years), adult (from about 18 years to about 65 years), and elder (from about 65 years until death).

As used herein, the term "immunocompromised" refers to a subject, e.g., a human, who is in a state in which the immune system's ability to fight an infection or disease is compromised or entirely absent. In one embodiment of the present disclosure, an aged or elderly subject, although not immunodeficient, may have a reduced capacity to generate an immune response to, for example, a pathogen.

A "biofilm" as used herein refers to an aggregate of microorganisms in which cells adhere to each other on a surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces, e.g., on catheters or other artificial implants. An "implant" or artificial implant" refers a medical device manufactured to replace a missing biological structure, support a damaged biological structure, or enhance an existing biological structure. Exemplary artificial implants include catheters, artificial hips, knees heart valves, and dental implants which may comprise pins, rods, screw and plates.

C5a ANALOGS

C5a is a protein fragment released from complement component C5. In humans, the polypeptide contains 74 amino acids (SEQ ID NO: 1). In one embodiment of the present disclosure, the C-terminus of C5a comprises amino acids 65-74 of C5a (i.e., ISHKDMQLGR ("C5a$_{65\text{-}74}$") (SEQ ID NO: 2). The disclosure further provides a C5a analog comprising 1, 2, 3, 4, or 5 amino acid substitutions in the amino acid set out in SEQ ID NO: 2 wherein the peptide having the substituted amino acid sequecne retains binding activity of the peptide set out in SEQ ID NO: 2.

The C-terminal analog of C5a EP54 (YSFKPMPLaR; SEQ ID NO: 3) has been described previously (Duryee et al. (2009) Vaccine 27:2981-2988; Hegde et al. (2008) Int. Immunopharmacol. 8:819-827; and Ulrich et al. (2000) J. Immunol. 164:5492-5498). However, these studies described and EP54 construct wherein EP54 was conjugated to a specific antigen or hapten. The disclosure further provides a C5a analog comprising 1, 2, 3, 4, or 5 amino acid substitutions in the amino acid sequence set out in SEQ ID NO: 3 wherein the peptide having the substituted amino acid sequecne retains binding activity of the peptide set out in SEQ ID NO: 3.

EP67 was derived from the C-terminal region of human complement component, C5a (Taylor S M, et al., Curr Med Chem 2001; 8:675-684.). EP67, YSFKDMP(MeL)aR (SEQ ID NO:4), (uppercase letters designate the L stereoisomeric form and lower case the D stereoisomeric form of the amino acids; (MeL) corresponds to N-methyl leucine) possess potent immune-enhancing properties (Morgan et al., Vaccine, 28(2): 463-469 (2009)). The disclosure further provides a C5a analog comprising 1, 2, 3, 4, or 5 amino acid substitutions in the amino acid sequence set out in SEQ ID NO: 4 wherein the peptide having the substituted amino acid sequence retains binding activity of the peptide set out in SEQ ID NO: 4.

Additional analogs are described, for example, in U.S. Pat. Nos. 5,696,230 and 6,821,517. U.S. Pat. No.5,696,230 describes that C-terminal peptide analogs of C5a, whose naturally flexible structure has been modified to constrain the peptides to specific conformations, are not only manyfold more potent than previously-described peptide analogs, but also exhibit the ability to selectively stimulate different classes of biological responses associated with C5a.

The present disclosure further relates to screening assays to identify C-terminal analogs of C5a, and the use of said analogs to treat or prevent infections or diseases as described herein. Binding activity of C-terminal analogs of C5a to CD88 is measured using standard techniques known in the art (See, e.g., U.S. Pat. No. 5,696,230). In various embodiments, C-terminal analogs of C5a of the present disclosure compete with naturally-occurring C5a or the C-terminus thereof for binding CD88 by more than 15%, more than 20%, more than 30%, more than 40%, more than 50%, more than 60%, more than 70%, more than 80%, or more than 90%.

In one aspect, the starting material of the present disclosure is a protein, oligopeptide or peptide. Oligopeptide molecules contemplated include biologically active fragments of a full length protein (e.g., a C-terminal fragment of C5a) as well as biologically active analogs, derivatives and variants of such oligopeptides. Thus, oligopeptides of the present disclosure include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 5, about 6, about 7, about 8, about 9, about 10, about 11, about 12, about 13, about 14, about 15, or about 20 or more amino acids, to an oligopeptide encoded by a referenced nucleic acid or an amino acid sequence described herein (e.g., C5a$_{65\text{-}74}$ or an oligopeptide C-terminal analog of C5a as provided herein), an immunogenic fragment thereof, and/or a conservatively modified analog, derivative and variant thereof.

An oligopeptide or peptide variant, for example, is a type of analog and refers to a oligopeptide or peptide sharing substantially similar structure and having the same biological activity as a reference oligopeptide or peptide or protein (i.e., "native oligopeptide or peptide" or "native therapeutic protein"). Variants differ in the composition of their amino acid sequences compared to the naturally-occurring or reference oligopeptide or peptide from which the variant is derived, based on one or more mutations involving (i) deletion of one or more amino acid residues at one or more termini of the oligopeptide or peptide and/or one or more internal regions of the naturally-occurring or reference oligopeptide or peptide sequence (e.g., fragments), (ii) insertion or addition of one or more amino acids at one or more termini (typically an "addition" or "fusion") of the oligopeptide or peptide and/or one or more internal regions (typically an "insertion") of the naturally-occurring or reference oligopeptide or peptide sequence or (iii) substitution of one or more amino acids for other amino acids in the naturally-occurring or reference oligopeptide or peptide sequence.

Variant oligopeptides or peptides include insertion variants, wherein one or more amino acid residues are added to a reference amino acid sequence of the present disclosure. Insertions may be located at either or both termini of the oligopeptide or peptide, and/or may be positioned within internal regions of the reference amino acid sequence. Insertion variants, with additional residues at either or both termini, include for example, fusion oligopeptides or peptides and oligopeptides or peptides including amino acid tags or other amino acid labels. In one aspect, the oligopeptide or peptide molecule optionally contains an N-terminal Met, especially when the molecule is expressed recombinantly in a bacterial cell such as E. coli.

In deletion variants, one or more amino acid residues in a reference amino acid sequence as described herein are removed. Deletions can be effected at one or both termini of the oligopeptide or peptide, and/or with removal of one or more residues within the reference amino acid sequence. Deletion variants, therefore, include fragments of a reference amino acid sequence.

In substitution variants, one or more amino acid residues of a reference amino acid sequence are removed and replaced with alternative residues. In one aspect, the substitutions are conservative in nature and conservative substitutions of this type are well known in the art. Alternatively, the present disclosure embraces substitutions that are also non-conservative. Exemplary conservative substitutions are described in Lehninger, [Biochemistry, 2nd Edition; Worth Publishers, Inc., New York (1975), pp.71-77] and are set out immediately below.

Conservative Substitutions

| SIDE CHAIN CHARACTERISTIC | AMINO ACID |
| --- | --- |
| Non-polar (hydrophobic): | |
| A. Aliphatic | A L I V P |
| B. Aromatic | F W |

-continued

| SIDE CHAIN CHARACTERISTIC | AMINO ACID |
| --- | --- |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

As described herein, in various embodiments, the oligopeptide is modified to introduce amino acid homologs or amino acid derivatives. By way of example, in various embodiments of the present disclosure, conformationally biased, response-selective oligopeptide C-terminal analogs of C5a are produced by the inclusion of amino acid homologs (e.g., to restrict backbone flexibility in order to bias features of peptide topography). Such amino acid homologs include, but are not limited to, D stereoisomeric forms of amino acids, Pro, N-methyl amino acids, acterio amino acids, and intramolecular cyclizations, including, for example and without limitation, side chain-to-side chain, side chain-to-backbone, and head-to-tail cyclizations.

Oligopeptide modifications may be accomplished using standard molecular biological techniques known in the art and can be accomplished recombinantly (e.g., engineering an amino acid sequence) such that the purified, modified oligopeptides comprise the desired sequence. Alternatively, such modification may be accomplished in vitro following or during the production and purification of the oligopeptide. For example, oligopeptide C-terminal analogs of C5a of the present disclosure may be prepared by various synthetic methods of peptide synthesis via condensation of one or more amino acid residues, in accordance with conventional peptide synthesis methods. Oligopeptide are synthesized according to standard solid-phase methodologies, such as may be performed on an Applied Biosystems Model 430A peptide synthesizer (Applied Biosystems, Foster City, Calif.) or AAPPTEC Apex Model 396 synthesizer, according to manufacturer's instructions. Other methods of synthesizing peptides, oligopeptides or peptidomimetics, either by solid phase methodologies or in liquid phase, are well known to those skilled in the art. When solid-phase synthesis is utilized, the C-terminal amino acid is linked to an insoluble carrier that can produce a detachable bond by reacting with a carboxyl group in a C-terminal amino acid. One preferred insoluble carrier is p-hydroxymethylphenoxymethyl polystyrene (HMP) resin. Other useful resins include, but are not limited to: phenylacetamidomethyl (PAM) resins for synthesis of some N-methyl-containing peptides (this resin is used with the Boc method of solid phase synthesis; and MBHA (p-methylbenzhydrylamine) resins for producing peptides having C-terminal amide groups, and Wang resins for utilization in Fmoc-based chemistries.

During the course of oligopeptide synthesis, branched chain amino and carboxyl groups may be protected/deprotected as needed, using commonly-known protecting groups. In one embodiment, $N^\alpha$-amino groups are protected with the base-labile 9-fluorenylmethyloxycarbonyl (Fmoc) group or t-butyloxycarbonyl (Boc groups). Side-chain functional groups consistent with Fmoc synthesis are protected as follows: arginine (2,2,5,7,8-pentamethylchroman-6-sulfonyl); asparagine (O-t-butyl ester); cysteine glutamine and histadine (trityl); lysine (t-butyloxycarbonyl); serine and tyrosine (t-butyl). An example of a preferred peptide synthetic method is set forth in Example 1 of U.S. Pat. No. 5,696,230, which is incorporated by reference in its entirety. Modification utilizing alternative protecting groups for peptides and peptide derivatives will be apparent to those of skill in the art.

In various embodiments of the invention, the C-terminal analogs of C5a described herein are cyclic (e.g., a ring system containing multiple amino acids and/or amino acid homologs and derivatives and/or intramolecular cyclizations) or acyclic (e.g., linear insofar as the N- and C-termini are not linked by, for example, a peptide bond, nor the presence of intermolecular cyclizations).

Nucleic acids encoding a C-terminal analog of C5a of the present disclosure include, for example and without limitation, gene fragments and associated pre-mRNAs, mRNAs, cDNAs, polymorphic variants, alleles, synthetic and naturally-occurring mutants.

Polynucleotides encoding a C-terminal analogs of C5a of the present disclosure also include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 60%, about 70%, about 75%, about 80%, about 85%, about 90%, about 95%, about 96%, about 97%, about 98%, about 99%, or higher nucleotide sequence identity, over a region of at least about 5, about 10, about 15, about 20, about 25, about 30, about 40, about 50, about 60, about 70, about 80, about 90, about 100, about 150, about 200, about 250, about 500, about 1000, or more nucleotides, to a reference nucleic acid sequence as described herein. Exemplary "stringent hybridization" conditions include hybridization at 42 Oc in 50% formamide, 5×SSC, 20 mM Na.PO4, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§ 9.47-9.51.

Microorganisms, Infections and Diseases

The selective activation of host innate immunity with a safe, well-designed immune stimulatory molecule such as one of the conformationally-biased, response-selective analogs of C5a 65-74 described herein would reduce the mutational pressures imposed by antibiotic therapy currently being employed and would be important for treating bacterial, fungal, and viral infections by stimulating host innate immunity. Such an approach induces host innate immune activation via the immunostimulatory portion of the complement pathway, rather than through pathogen-associated molecular pattern (PAMP) or Toll-like receptors. Thus, such analogs will be effective against pathogens that may develop defenses to skirt immune activation via PAMPs. As an immunotherapeutic, such analogues can be used with other conventional therapies to complement their activity and enhance the overall outcome.

In one embodiment, these C-terminal analogs of C5a are synthetic products. As such, C-terminal analogs of C5a overcome many manufacturing issues required to accommodate rapid distribution to a world-wide population. These analogs are simple to synthesize and purify in large quantities; it is characterized at the molecular level; it is generated as a dry powder and purified via standard HPLC methods without risk of associated DNA, RNA, or bacterial contamination. This powder is stable for years at room temperature. This allows for convenient distribution to the clinic where it can be dissolved immediately prior to use. At no point in manufacture, distribution, or storage is refrigeration or the use of preservatives required.

Host innate immunity is the first line of defense in controlling infections. It occurs rapidly and is not necessarily antigen specific. It provides a broad spectrum defense mechanism for acute infections. Acquired immunity is a result of exposing the host to the pathogen or a component of the pathogen in the form of a vaccine that then allows the host to develop a long lasting immune response (both humoral and/or cell mediated) to the specific pathogen. In various embodiments, the C-terminal analogs of C5a described herein induces host innate immunity and/or acquired immunity. The ability to induce innate immunity in a non-antigen-specific method has advantages in that it affords induction of immune responses to a wide range of pathogens irrespective of the nature of the antigens these pathogens express. Thus, the ability to induce a protective immune response is not dependent upon reaction to a specific antigen expressed by a pathogen, but rather to the pathogen itself.

As described herein, the ability to induce innate immunity in a non-antigen-specific method has advantages in that it affords induction of immune responses to a wide range of pathogens irrespective of the nature of the antigens these pathogens express. Thus, the ability to induce a protective immune response is not dependent upon reaction to a specific antigen expressed by a pathogen, but rather to the pathogen itself.

The overuse of antibiotics for treating infections has created mutational pressures that have facilitated an alarming rise in resistant bacteria, which has outpaced the development of new antibiotics to treat them. The ability to treat these infections is not only a major public health concern, but also presents an urgently needed capability that provides security against bioterrorism and the potential of an intended release of "superbugs" that may be manufactured to evade traditional anti-bacterial therapies.

The analogs of the present disclosure represent, in various embodiments, a therapeutic molecule to treat or prevent infections or diseases associated with, and/or directly kill, a variety of microorganisms or infectious particles, including but not limited to bacteria, virus, fungus, parasite, protozoan, prion, cancer cells, or other transformed cells. In one embodiment, the infection is caused by an antibiotic-resistant microorganism, such as bacteria. In still another embodiment, the therapeutic molecule is used to control bacterial burdens associated with a biofilm.

The analogs of the present disclosure represent, in various embodiments, a therapeutic molecule to treat or prevent, either by direct killing or by activating a host immune response, a variety of diseases and infections, including but not limited to those that relate to the respiratory system, such as obstructive lung diseases (e.g., emphysema, bronchitis, asthma, chronic obstructive pulmonary disease, bronchiectasis, byssinosis, bronchiolitis, asbestosis, restrictive lung diseases such as fibrosis, cystic fibrosis, sarcoidosis, alveolar damage, pleural effusion, hypersensitivity pneumonitis, pleurisy, lung cancer, infectious lung diseases such as influenza, upper respiratory tract infections, lower respiratory tract infections or pneumonias, tuberculosis, vascular lung diseases such as pulmonary edema, pulmonary embolism, pulmonary hypertension, and respiratory tumors), those that are inflammatory-related such as rheumatoid arthritis, restenosis, asthma, Crohn's disease, incontinentia pigmenti, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, and infection.

The analogs of the present disclosure represent, in various embodiments, a therapeutic molecule to treat or prevent, either by direct killing or by activating a host immune response, an infectious disease including, but not limited to, Acinetobacter infections, Actinomycosis, African sleeping sickness (African trypanosomiasis), AIDS (Acquired immune deficiency syndrome), Amebiasis, Anaplasmosis, Anthrax, Arcanobacterium haemolyticum infection, Argentine hemorrhagic fever, Ascariasis, Aspergillosis, Astrovirus infection, Babesiosis, *Bacillus cereus* infection, Bacterial pneumonia, Bacterial vaginosis (BV), Bacteroides infection, Balantidiasis, Baylisascaris infection, BK virus infection, Black acter, Blastocystis hominis infection, Blastomycosis, Bolivian hemorrhagic fever, Borrelia infection, Botulism (and Infant botulism), Brazilian hemorrhagic fever, Brucellosis, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, chickenpox, Chlamydia, *Chlamydophila pneumoniae* infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem acteri, Fasciolopsiasis, Fasciolosis, Fatal familial insomnia (FFI), Filariasis, Food poisoning by *Clostridium perfringens*, Free-living amebic infection, Fusobacterium infection, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, Haemophilus influenzae infection, Hand, foot and mouth disease (HFMD), Hantavirus Pulmonary Syndrome (HPS), Helicobacter pylori infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Mastitis, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Prevotella infection, Primary amoebic meningoencephalitis (PAM), Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans (OLM)), Toxocariasis (Visceral Larva Migrans (VLM)), Toxoplasmosis, Trichinellosis, Trichomoniasis, Trichuriasis (Whipworm infection), Tuberculosis, Tularemia, Ureaplasma urealyticum infection, Venezuelan equine encephalitis, Venezuelan hemorrhagic fever, Viral pneumonia, West Nile Fever, White acter (Tinea blanca), Yersinia pseudotuberculosis infection, Yersiniosis, Yellow fever, and Zygomycosis.

The analogs of the present disclosure represent, in various embodiments, a therapeutic molecule to treat or prevent, either by direct killing or by activating a host immune response, a subject infected with a pathogen (and their associated diseases) including, but not limited to, cytomegalovirus (autism, autoimmune diseases, brain tumor, dementia, diabetes mellitus type 2, Guillain-Barré syndrome, lupus, metabolic syndrome, myocardial infarction), enteroviruses (amyotrophic lateral sclerosis, ADHD, autoimmune diseases, carcinoid tumors, chronic fatigue syndrome, diabetes mellitus type 1, diabetes mellitus type 2, Guillain-Barré syndrome, myocardial infarction, schizophrenia), Epstein-Barr virus (autoimmune diseases, breast cancer, esophageal cancer, Hodgkin's lymphoma, nasopharyngeal carcinoma, chronic obstructive pulmonary disease, seasonal affective disorder, lupus, multiple sclerosis), Hepatitis B virus (hepatocellular carcinoma, pancreatic cancer, vasculitis), Hepatitis C virus (Hodgkin's lymphoma, hepatocellular carcinoma, diabetes mellitus type 2, vasculitis), Herpes simplex virus (Alzheimer's disease, coronary heart disease, metabolic syndrome), HIV (ADHD, autoimmune diseases, Hodgkin's lymphoma, Kaposi's Sarcoma, non-Hodgkin lymphoma, dementia, vasculitis), Human herpesvirus 6 (ADHD, chronic fatigue syndrome, epilepsy, multiple sclerosis), Influenza A (ADHD, Parkinson's disease), Parvovirus B19 (autoimmune diseases, chronic fatigue syndrome, lupus, rheumatoid arthritis, vasculitis), Bartonella (major depressive disorder, panic disorder), Borrelia (anorexia nervosa, ADHD, bipolar disorder, dementia, depression, obsessive-compulsive disorder, rheumatoid arthritis, sarcoidosis, schizophrenia), Chlamydia pneumonia (Alzheimer's disease, asthma, atherosclerosis, lung cancer, chronic fatigue syndrome, chronic obstructive pulmonary disease, coronary heart disease, metabolic syndrome, multiple sclerosis, myocardial infarction, stroke, Tourette's syndrome), *Helicobacter pylori* (Alzheimer's disease, autoimmune diseases, pancreatic cancer, stomach cancer, metabolic syndrome, obesity, soriasis, sarcoidosis, stroke), *Mycobacterium tuberculosis* (autoimmune diseases, depression, stroke), *Streptococcus* (anorexia nervosa, ADHD, colorectal cancer, obsessive-compulsive disorder, Tourette's syndrome), and *Toxoplasma gondii* (Alzheimer's disease, depression, Parkinson's disease, Tourette's syndrome).

The analogs of the present disclosure represent, in various embodiments, a therapeutic molecule to treat or prevent, either by direct killing or by activating a host immune response, infections or diseases associated with a variety of infections caused by bacteria including, but not limited to, antibiotic-resistant bacteria such as methicillin-resistant *S. aureus* (MRSA), including health care-associated MRSA (HA-MRSA) and community associated MRSA (CA-MRSA), and MRSA strain USA300-FPR3757, vancomycin-resistant *S. aureus* (VRSA), *S. pyogenes* e.g., resistant to macrolide, penicillin-resistant pneumonia caused by *Streptococcus pneumoniae* (commonly known as pneumococcus), *Mycobacterium tuberculosis* (commonly resistant to isoniazid and rifampin) and Extensively Drug-Resistant Tuberculosis (XDR TB), multidrug-resistant Enterococcus faecalis and *Enterococcus faecium*, *Pseudomonas aeruginosa*, *Clostridium difficile* (e.g., clindamycin-resistant and fluoroquinolone antibiotics), *Acinetobacter baumannii*, and any antibiotic-resistant strain of bacteria described herein.

The analogs of the present disclosure represent, in various embodiments, a therapeutic molecule to treat or prevent, either by direct killing or by activating a host immune response, infections or diseases associated with, and/or directly kill, a variety of infections caused by bacteria including, but not limited to, *Acinetobacter baumannii*, *Bacillus anthraces, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia acteriost, Salmonella typhi, Salmonella typhimurium, Shigella sonnei, Staphylococcus aureus, Staphylococcus epidermidis, Staphylococcus saprophyticus, Streptococcus agalactiae, Streptococcus mutans, Streptococcus pneumoniae, Streptococcus pyogenes, Treponema pallidum, Vibrio cholerae*, and *Yersinia pestis*.

The analogs of the present disclosure also represent, in various embodiments, a therapeutic molecule to control, prevent or treat, either by direct killing or by activating a host immune response, biofilms associated, for example, with catheters or other artificial implants. Such biofilms are caused, in various embodiments, by bacteria including, but not limited to, *Pseudomonas aeruginosa, Streptococcus mutans, Streptococcus sanguinis, Legionella, Neisseria gonorrhoeae*, and *Staphylococcus aureus*.

The analogs of the present disclosure represent, in various embodiments, a therapeutic molecule to treat or prevent, either by direct killing or by activating a host immune response, infections or diseases associated with a variety of infections or diseases caused by viruses including, but not limited to, Poxviridae, Chordopoxvirinae, Orthopoxvirus, Cowpoxvirus, Monkeypox virus, Vaccinia virus, Variola virus, Parapoxvirus, Bovine acteri stomatitis virus, Orf virus, Pseudocowpox virus, Molluscipoxvirus, Molluscum contagiosum virus, Yatapoxvirus, Tanapox virus, Yaba monkey tumor virus, Herpesviridae, Alphaherpesvirinae, Simplexvirus, Human herpesvirus 1, Herpes simplex virus 1, Human herpesvirus 2, Herpes simplex virus 2, Varicellovirus, Human herpesvirus 3, Varicella-zoster virus, Betaherpesvirinae, Cytomegalovirus, Human herpesvirus 5, Human cytomegalovirus, Roseolovirus, Human herpesvirus 6, Human herpesvirus 7, Gammaherpesvirinae, Lymphocryptovirus, Human herpesvirus 4, Epstein-Barr virus, Rhadinovirus, Human herpesvirus 8, Kaposi's sarcoma-associated herpesvirus, Adenoviridae, Mastadenovirus, Human adenovirus A, Human adenovirus B, Human adenovirus C, Human adenovirus D, Human adenovirus E, Human adenovirus F, Polyomaomaviridae, Polyomavirus, BK polyomavirus, Human polyomavirus, JC polyomavirus, Papillomaviridae, Alphapapillomavirus, Human papillomavirus 2, Human papillomavirus 10, Human papillomavirus 6, Human papillomavirus 7, Human papillomavirus 16, Human papillomavirus 18, Human papillomavirus 26, Human papillomavirus 32, Human papillomavirus 34, Human papillomavirus 53, Human papillomavirus 54, Human papillomavirus 61, Human papillomavirus 71, Human papillomavirus cand90, Betapapillomavirus, Human papillomavirus 5, Human papillomavirus 9, Human papillomavirus 49, Human papillomavirus cand92, Human papillomavirus cand96, Gammapapillomavirus, Human papillomavirus 4, Human papillomavirus 48, Human papillomavirus 50, Human papillomavirus 60, Human papillomavirus 88, Mupapillomavirus, Human papillomavirus 1, Human papillomavirus 63, Parvoviridae, Parvovirinae, Erythrovirus, B19 virus, Hepadnaviridae, Orthohepadnavirus, Hepatitis B virus, Retroviridae, Orthoretrovirinae, Deltaretrovirus, Primate T-lymphotropic virus 1, Primate T-lymphotropic virus 2, Lentivirus, Human immunodeficiency virus 1, Human immunodeficiency virus 2, Reoviridae, Orthoreovirus, Mammalian orthoreovirus, Orbivirus, African horse sickness virus, Changuinola virus, Corriparta virus, Orungo virus, Rotavirus, Rotavirus A, Rotavirus B, Mononegavirales, Filoviridae, Marburgvirus, Lake Victoria acteriostat, Ebolvirus, Ivory Coast ebolavirus, Reston ebolavirus, Sudan ebolavirus, Zaire ebolavirus, Paramyxoviridae, Paramyxovirinae, Respirovirus, Human parainfluenza virus 1, Human parainfluenza virus 3, Morbillivirus, Measles virus, Edmonston virus, Rubulavirus, Human parainfluenza virus 2, Human parainfluenza virus 4, Mumps virus, Henipavirus, Hendravirus, Nipahvirus, Pneumovirinae, Pneumovirus, Human respiratory syncytial virus, Metapneumovirus, Human metapneumovirus, Rhabdoviridae, Vesiculovirus, Chandipura virus, Cocal virus, Isfahan virus, Piry virus, Vesicular stomatitis Alagoas virus, Vesicular stomatitis Indiana virus, Vesicular stomatitis New Jersey virus, Lyssavirus, Australian bat lyssavirus, Rabies virus, Orthomyxoviridae, Influenzavirus A, Influenza A virus, Influenzavirus B, Influenza B virus, Influenzavirus C, Influenza C virus, Bunyaviridae, Bunyavirus, Bunyamwera virus, Bwamba virus, California encephalitis virus, Guama virus, Oriboca virus, Oropouche virus, Hantavirus, Andes virus, Hantaan virus, Puumala virus, Seoul virus, Dobrava-Belgrade virus, Bayou virus, Black Creek Canal virus, New York virus, Sin Nombre virus, Nairovirus, Crimean-Congo hemorrhagic fever virus, Nairobi sheep disease virus, Phlebovirus, Rift Valley fever virus, Sandfly fever Naples virus, Arenaviridae, Arenavirus, Lassa virus, Lymphocytic choriomeningitis virus, Guanarito virus, Junín virus, Machupo virus, Sabiávirus, Deltavirus, Hepatitis delta virus, Nidovirales, Coronaviridae, Coronavirus, Human coronavirus 229E, Human coronavirus OC43, Human enteric coronavirus, Severe acute respiratory acterio coronavirus, Torovirus, Picornaviridae, Enterovirus, Human enterovirus A, Human enterovirus B, Human enterovirus C, Human enterovirus D, Poliovirus, Rhinovirus, Human rhinovirus A, Human rhinovirus B, Hepatovirus, Hepatitis A virus, Parechovirus, Human parechovirus, Caliciviridae, Norovirus, Norwalk virus, Sapovirus, Sapporo virus, Hepevirus, Hepatitis E virus, Astroviridae, Mamastrovirus, Human astrovirus, Togaviridae, Alphavirus, Chikungunya virus, O'nyong-nyong virus, Mayaro virus, Ross River virus, Barmah Forest virus, Sindbis virus, Ockelbo virus, Venezuelan equine encephalitis virus, Western equine encephalitis virus, Eastern equine encephalitis virus, Rubivirus, Rubella virus, Flaviviridae, Flavivirus, Kyasanur Forest disease virus, Omsk hemorrhagic fever virus, Powassan virus, Louping ill virus, Tickborne encephalitis virus, Dengue virus, Japanese encephalitis virus, Murray Valley encephalitis virus, St. Louis encephalitis virus, West Nile virus, Ilheus virus, Yellow fever virus, Apoi virus, Hepacivirus, Hepatitis C virus, GB virus B, and GB virus A.). In various embodiments, the infection or disease is caused by influenza A or human immunodeficiency virus (HIV).

The analogs of the present disclosure represent, in various embodiments, a therapeutic molecule to treat or prevent, either by direct killing or by activating a host immune response, infections or diseases associated with a variety of fungal infections including, but not limited to, *Candida* (e.g., *C. albicans*), *Aspergillus* (e.g., *A. fumigates, A. flavus*, and *A. clavatus*), *Cryptococcus* (e.g., *C. neoformans, C. laurentii, C. albidus*, and *C. gatti*), *Histoplasma* (e.g., *H. capsulatum*), *Pneumocystis* (e.g., *P. jirovecii*), *Stachybotrys* (e.g., *S. chartarum*), and *Coccidioides* (e.g., *C. immitis* and *C. posadasii*).

The analogs of the present disclosure represent, in various embodiments, a therapeutic molecule to treat or prevent, either by direct killing or by activating a host immune response, infections or diseases associated with a variety of parasitic organisims and/or infections including, but not limited to, protozoans, helminthes, parasitic worms, Halzoun syndrome, myiasis, Chogoe fly, human botfly, candiru, bedbug, head louse, body louse, crab louse, demodex, scabies, and screwworm. Further, the analogs of the present disclosure represent, in various embodiments, a therapeutic approach to treat or prevent infections or diseases associated with, and/or directly kill, a variety of protozoans and or protozoan infections including, but not limited to, *Entamoeba Histolytica, Giardia Lambda, Trichomonas Vaginalis, Trypanosoma Brucei, T. Cruzi, Leishmania Donovani, Balantidium Coli, Toxoplasma Gondii, Plasmodium* Spp., *Babesia Microti*, acanthamoeba, babesiosis, balantidiasis, blastocystosis, coccidia, dientamoebiasis, amoebiasis, giardia, isosporiasis, leishmaniasis, primary amoebic meningoencephalitis (PAM), malaria, rhinosporidiosis, toxoplasmosis (parasitic pneumonia), trichomoniasis, sleeping sickness, and Chagas disease.

The analogs of the present disclosure represent, in various embodiments, a therapeutic molecule to treat or prevent, either by direct killing or by activating a host immune response, diseases associated with infectious particles such as prions including, but not limited to, scrapie, bovine spongiform encephalopathy (BSE, mad cow disease), transmissible mink encephalopathy, chronic wasting disease, feline spongiform encephalopathy, exotic ungulate encephalopathy, Creutzfeldt-Jakob disease, iatrogenic Creutzfeldt-Jakob disease, variant Creutzfeldt-Jakob disease, familial Creutzfeldt-Jakob disease, sporadic Creutzfeldt-Jakob disease, Gerstmann-Straussler-Scheinker syndrome, fatal familial insomnia, and Kuru.

The analogs of the present disclosure also represent, in various embodiments, a therapeutic approach to treat a subject (e.g., human) that has multiple diseases or infections or, in various embodiments, treating one or more than one infection or disease while also preventing additional infections or diseases, either by direct killing or by activating a host immune response.

Compositions and Methods of Administering

In various embodiments of the present disclosure, a composition comprising one or more "therapeutic agents" or "active agent," e.g., a C-terminal analog of C5a, is provided.

In various embodiments, the composition comprises a pharmaceutically acceptable carrier, e.g., one or more solvents, dispersion media, coatings, antibacterial and antifungal agents, isotonic and absorption delaying agents, and the like, compatible with administration to a mammal, such as a human. Any carrier compatible with the excipient(s) and therapeutic agent(s) (e.g., C-terminal analog of C5a) is suitable for use. Supplementary active compounds may also be incorporated into the compositions. A composition of the present disclosure is formulated to be compatible with its intended route of administration. Examples of routes of administration include oral administration (ingestion) and parenteral administration, e.g., intravenous, intradermal, subcutaneous, inhalation, nasal, transdermal (topical), transmucosal, buccal, sublingual, pulmonary and rectal administration. Solutions or suspensions used for parenteral application may include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH may be adjusted with acids or bases, such as hydrochloric acid or sodium hydroxide.

Oral compositions generally include an inert diluent or an edible carrier. Oral formulations generally take the form of a pill, tablet, capsule (e.g., softgel capsule, solid-filled capsule, or liquid-filled capsule), solid lozenge, liquid-filled lozenge, mouth and/or throat drops or spray, effervescent tablets, orally disintegrating tablet, suspension, emulsion, syrup, elixir, or tincture. The composition may be contained in enteric forms to survive the stomach or further coated or mixed to be released in a particular region of the gastrointestinal tract by known methods. Solid oral dosage forms are typically swallowed immediately, or slowly dissolved in the mouth. Oral compositions may also be prepared using a fluid carrier for use as a mouthwash, wherein the compound in the fluid carrier is applied orally and swished and expectorated or swallowed. Oral formulations optionally contain any of the following ingredients, or compounds of a similar nature: a binder such as microcrystalline cellulose, gum tragacanth or gelatin; starch or lactose; a disintegrating agent such as alginic acid, Primogel™, or corn starch; a lubricant such as magnesium stearate; a glidant such as colloidal silicon dioxide; and/or a sweetening agent such as sucrose or saccharin.

For administration by inhalation, the composition is optionally delivered in the form of a spray. The spray may be an aerosol spray from a pressured container or dispenser, which contains a suitable propellant, e.g., a gas such as carbon dioxide, or a nebulizer. The composition is optionally formulated for delivery via a dry powder inhaler (DPI), a metered dose inhaler (pMDI), nasal spray, or a vaporizer. For routes of administration involving absorption of an agent and/or excipient through mucosal membrane, the composition further optionally comprises a penetrant.

Optionally, the composition is formulated as a "liquid respiratory composition," i.e., a composition in a form that is deliverable to a mammal via the oral cavity, mouth, throat, nasal passage or combinations thereof. These compositions can be delivered by a delivery device selected from droppers, pump, sprayers, liquid dropper, spoon, cup, squeezable sachets, power shots, and other packaging and equipment, and combinations thereof. In one embodiment, the liquid respiratory composition comprises the therapeutic agent, and excipient, a thickening polymer (e.g., xanthan gum, cellulosic polymers such as carboxymethy cellulose (CMC), hy droxyethylcellulose, hy droxymethylcellulose, and hydroxypropylmethylcellulose, carrageenan, polyacrylic acid, cross-linked polyacrylic acid such as Carbopol®, polycarbophil, alginate, clay, and combinations thereof), and optionally a mucoadhesive polymer (e.g., polyvinylpyrrolidone (Povidone), methyl vinyl ether copolymer of maleic anhydride (Gantrez®), guar gum, gum tragacanth, polydextrose, cationic polymers, poly(ethylene oxide), poly(ethylene glycol), poly(vinyl alcohol), poly(acrylic acid), cross-linked polyacrylic acid such as Carbopol®, polycarbophil, poly(hydroxyl ethyl methacrylate), chitosan, cellulosic polymers such as carboxymethycellulose (CMC), hydroxyethylcellulose, hydroxymethylcellulose, and hydroxypropylmethylcellulose, and combinations thereof). The composition is preferably a non-Newtonian liquid that exhibits zero shear viscosity from about 100 centiPoise (cP) to about 1,000,000 cP, from about 100 cP to about 500,000 cP, from about 100 cP to about 100,000 cP, from about 100 cP to about 50,000 cP, from about 200 cP to about 20,000 cP, from about 1,000 to about 10,000 cP at a temperature of about 37° C., as measured according to the Shear Viscosity Method. The pH range of the formulation is generally from about 1 to about 7, from about 2 to about 6.5, and from about 4 to about 6.

In various embodiments, in addition to the excipient(s) and therapeutic agent(s) described herein, a nasal spray formulation comprises benzalkonium chloride, camphor, chlorhexidine gluconate, citric acid, disodium EDTA, eucalyptol, menthol, purified water, and/or tyloxapol. An exemplary oral composition comprises FD&C Blue No. 1, gelatin, glycerin, polyethylene glycol, povidone, propylene glycol, purified water, sorbitol special, and/or titanium dioxide in addition to an excipient and acetaminophen, doxylamine succinate, and phenylephrine HCl (or dextromethorphan).

Pharmaceutical compositions suitable for injectable use include sterile aqueous solutions (where water-soluble), or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition is sterile and fluid to allow syringability. The carrier may be a solvent or dispersion medium containing, for example, water, ethanol, polyol (for example, glycerol, propylene glycol, and liquid polyethylene glycol, and the like), and suitable mixtures thereof. Fluidity is maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions may be brought about by including in the composition an agent that delays absorption, for example, aluminum monostearate and gelatin. The injectable preparations may be enclosed in ampules, disposable syringes or multiple dose vials made of glass or plastic.

In various embodiments of the present disclosure, powders, creams and gels are contemplated for topical administration of a pharmaceutical composition. In one embodiment, the topical administration refers to the application of a therapeutic composition to a localized area of the body or to the surface of a body part where action or symptom relief is desired. In one embodiment, a transdermal patch is used according the present disclosure. In still other embodiments, a pharmaceutical composition according to the present disclosure is embedded, e.g., in wound dressings, bandages (e.g., hydrocolloids, hydrogels, alginates, foams, gauze), and/or surgical sutures to prevent and/or treat infections and improve wound (e.g., scrapes, cuts, and surgical incisions) healing.

In one embodiment, the components of the composition are prepared with carriers that will protect the components against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid.

The formulation is provided, in various aspects, in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms are dictated by and are directly dependent on the unique characteristics of the excipient(s) and therapeutic agent(s) and the particular biological effect to be achieved.

Safety and efficacy of compositions described herein are determined by standard procedures using in vitro or in vivo technologies, such as the materials and methods described herein. Administration may be on an as-needed or as-desired basis, for example, once-monthly, once-weekly, or daily, including multiple times daily, for example, at least once daily, from one to about ten times daily, from about two to about four times daily, or about three times daily. A dose of composition optionally comprises about from about 0.001 mg to about 1000 mg active agent, alternatively from about 2.5 mg to about 750 mg active agent, and alternatively from about 5 mg to about 650 mg of the active agent. In one embodiment, a dose of composition according to the present disclosure comprises about from 0.1 mg to about 0.25 mg. In various embodiments, a dose of composition according to the present disclosure comprises 25 µg, 50 µg, 60 µg, 70 µg, 80 µg, 90 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg or 500 µg. In various embodiments, a dose of composition according to the present disclosure comprises between 25 µg to 500 µg, 50 µg to 400 µg, 100 µg to 300 µg, or 200 µg to 250 µg.

In various embodiments, a therapeutic agent, or a pharmaceutical composition comprising a therapeutic agent, is used in combination with one or more other active agents useful for treating or preventing infections or diseases. The other active agent(s) can enhance the effects of the therapeutic agent and/or exert other pharmacological effects in addition to those of the therapeutic agent. Non-limiting examples of active agents that can be used in combination with a therapeutic agent are immunosuppressants (e.g., cyclosporine, azathioprine), corticosteroids, anti-inflammatory agents, chemotherapeutic agents, antibiotics, antifungals, antivirals and antiparasitics. As described herein, other exemplary active agents that are contemplated include vaccines (e.g., existing vaccines directed to a specific pathogen or disease) and vaccines comprising C-terminal analogs of C5a conjugated to a specific antigen.

To achieve a desired therapeutic outcome in a combination therapy, a therapeutic agent such as a C-terminal analog of C5a and other active agent(s) are generally administered to a subject in a combined amount effective to produce the desired therapeutic outcome (e.g., reduction or elimination of one or more symptoms). The combination therapy can involve administering the C-terminal analog of C5a and the other active agent(s) at about the same time. Simultaneous administration can be achieved by administering a single composition that contains both the C-terminal analog of C5a and the other active agent(s). Alternatively, the other active agent(s) can be taken separately at about the same time as a pharmaceutical formulation comprising the C-terminal analog of C5a.

In other alternatives, administration of the therapeutic agent such as a C-terminal analog of C5a can precede or follow administration of the other active agent(s) by an interval ranging from minutes to hours. In embodiments where the C-terminal analog of C5a and the other active agent(s) are administered at different times, the C-terminal analog of C5a and the other active agent(s) are administered within an appropriate time of one another so that both the C-terminal analog of C5a and the other active agent(s) can exert a beneficial effect (e.g., synergistically or additively) on the recipient. In some embodiments, the C-terminal analog of C5a is administered to the subject within about 0.5-12 hours (before or after), or within about 0.5-6 hours (before or after), of the other active agent(s). In certain embodiments, the C-terminal analog of C5a is administered to the subject within about 0.5 hour or 1 hour (before or after) of the other active agent(s).

A "booster" dose of a C-terminal analog of C5a or a pharmaceutical composition comprising a C-terminal analog of C5a, separately or in combination with another active agent as described above, is also contemplated by the present disclosure. A booster dose may be administered about 1 week, about 1 month, about 2 months, about 3 months, about 4 months, about 5 months, about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years, about 15 years, and about 20 years after an initial administration.

The invention is further described in the following examples. The example serves only to illustrate the invention and are not intended to limit the scope of the invention in any way.

EXAMPLE 1

Intranasal Administration of a C-terminal Analog of C5a Induces Innate Immunity in the Lungs and Enhances Airway Immune Responsiveness The lung possesses a robust ability to induce innate immune responses to inhaled pathogens. Induction is controlled by both the alveolar macrophage (AM) and the bronchial epithelium (BE). Thus, experiments were designed to examine induction of pulmonary innate immunity with EP67.

In short, EP67 (3 mg/kg) was delivered directly to the lungs of mice through insufflation (IN). Animals were sacrificed one day later. Lungs were lavaged with PBS to isolate the bronchoalveolar lavage (BAL) cells for staining and FACS analysis.

Results showed that greater than 90% of the BAL cells isolated from an animal treated with saline alone were AM. This population, defined as large, highly autofluorescent, $CD11b^-CD11^+$, makes up most of the BAL cells in a normal lung. Insufflation of EP67 resulted in the appearance of cells bearing the $CD11b^+CD11c^+$ phenotype of exudate macrophages (exMac). Furthermore, a large population of $CD11b^+$ $CD11c^-$ cells appeared in the alveolar space. Further staining indicated that these cells were $GR-1^+$ neutrophils (not shown). Analysis of MHCII expression on all cell populations indicated that the $CD11c^{mid}$ $CD11b^{hi}$ cells (in the green rectangle) are the myeloid dendritic cells.

The time course of the EP67 response in the BAL cells showed that by seven days post EP67 administration, the neutrophils were largely lost and the AM are again the dominant BAL cell population. The EP67-induced changes in the BAL populations displayed a strict dose-response.

The innate immune responses to influenza is initiated with the release of proinflammatory chemokines and the recruitment of neutrophils, lymphocytes, and particularly mononuclear phagocytes into the alveolar air space to limit viral spread. The EP67-induced appearance of neutrophils and exMacs into the alveolar spaces thus mirrored the innate immune response to influenza. However, the innate immune response to influenza is normally delayed for up to 48 hours after infection influenza A, due to the viral nonstructural (NS)1 protein antagonism of host innate immunity.

To test the robustness of the EP67 response, mice were treated at the time of influenza infection. Animals were sacrificed one day later for analysis of BAL cells as above.

BAL cells from the mouse infected with influenza A/PR/8 24 hours earlier showed no induction of innate immunity at the cellular level. The majority of the cells were AM, with no obvious influx of either exMAcs or neutrophils. The EP67 treated animals displayed this influx of innate effectors. The animals that were infected with EP67 and simultaneously treated with EP67 showed a similar increase in BAL exMAcs and neutrophils to the uninfected animals treated with EP67. These results showed that the EP67 response is not negatively regulated by the viral NS1 protein.

Based on the robust response to EP67 even in the presence of concurrent influenza infection, the ability of EP67 to mitigate influenza pathogenesis was examined. Mice were infected with a non-lethal dose of influenza A/A/PR/8 and treated one time with EP67. Treatment was given either the day before infection, at the time of infection, or on day 1, 2, or 3 after infection. Animals were weighed daily for two weeks to follow disease progression and resolution.

The standard measure for non-lethal influenza morbidity is weight loss of ~20%, with a maximum at ~day 8 post-infection, followed by a rapid recovery. This pattern was displayed by the animals that did not receive EP67. Animals that were treated with EP67 either the day before infection or the day of infection lost significantly less weight than the non-treated animals. More surprisingly, the animals treated one day after infection also displayed significant protection from influenza-induced weight loss. Treatment with EP67 on days 2 or 3 after infection, (by which time the host innate immune response has been initiated and viral replication is near its maximum), was not associated with any protection from influenza-induced morbidity. These results indicated that EP67 is able to block influenza-induced illness either prior to infection (i.e., prophylaxis), and following exposure to a productive infection (emergency therapy).

All groups did show some evidence of weight loss at day 8 post-infection. This implied that the viral infection had been reduced but not completely eliminated.

To confirm that productive infection had taken place, an ELISA was performed for anti-influenza antibodies on the serum from these animals. If EP67 had completely blocked infection, there should not have been a strong anti-influenza Ab response. Instead, a high concentration of anti-influenza Abs was found in each group. The results show that EP67 treatment converted a pathogenic infection into a subclinical, immunizing infection. This development of acquired immunity can thus prevent illness following any subsequent exposure to the same organism.

The elderly, who suffer the vast majority of influenza-related morbidity and mortality, have an urgent and currently unmet need for better influenza therapeutics. More than 90% of influenza related deaths are found in the elderly population, making protection of this vulnerable population a critical goal. EP67-mediated protection of the elderly would therefore fill a major unmet health need. Since the aged mouse is considered a strong model for age-related changes in human immunity, the response of aged mice to EP67 insufflation was examined.

EP67 induces a large population of exMAcs and neutrophils into the alveolar space in aged lung as in lung. This indicates that EP67 can protect the vulnerable aged population.

EXAMPLE 2

Control of Methicillin-resistant S. aureus Infection Using a C-terminal Analog of C5a Staphylococcus aureus is a formidable human pathogen responsible for a variety of disease pathologies ranging from minor skin irritations to more severe infections such as septicemia, necrotizing pneumonia and necrotizing fasciitis. The emergence of multi-drug resistant strains of S. aureus, including community-acquired methicillin-resistant S. aureus (CA-MRSA), has increased the interest in the development of new vaccines and effective treatment strategies.

Using a murine necrotic skin lesion model, the present example demonstrates that administration of EP67 effectively limits CA-MRSA lesion formation and reduces the bacterial load at the site of infection. EP67 treatment resulted in increased cytokine production and neutrophil influx, which was required for controlling disease progression.

Bacterial strains and culture conditions. Methicillin-sensitive Staphylococcus aureus (MSSA) laboratory strain ISP479C (Pattee P A., et al., J Bacteriol 1981;145:479-488) and CA-MRSA USA300 isolate (TCH1516-HOU-MR, ATCC accession number BAA-1717) (Highlander S K, et al., BMC Microbiol 2007;7:99) were used in this study. Strains were grown aerobically in tryptone soy (TS) broth (Oxoid) at 37° C.

Peptide synthesis. EP67 [YSFKDMP(MeL)aR (SEQ ID NO: 4)] and the inactive control peptide scrambled EP67 (sEP67) [(MeL)RMYKPaFDS (SEQ ID NO: 5)] were synthesized by solid-phase methods as described previously (Taylor S M, Curr Med Chem 2001;8:675-684). Peptides were purified by analytical and preparative reverse-phase HPLC on C18-bonded silica columns with 0.1% TFA as the running buffer and 60% acetonitrile in 0.1% TFA as the eluant. Peptides were characterized by molecular mass (MH+) with MALDI mass spectrometry.

Mouse model of MRSA demonecrotic infection. All animal work was carried out under the approval of the Office of Laboratory Animal Care (OLAC) at San Diego State University and adhered to accepted veterinary standards. Outbred female CD1 mice 8-12 weeks of age were obtained from Charles River Laboratories. CD88−/− mice were purchased from Jackson Labs. Originally on a heterozygous background, these animals were back-crossed at least 5 times onto the C57B$^1/_6$ background. Prior to infection, hair was removed from the lower backs of mice (n=6-10) using a razor and depilatory cream. Sub-cutaneous S. aureus infection was carried out as described previously (Bunce C, et al., Infect Immun 1992;60:2636-2640). Briefly, 0.1 mL volumes of mid-logarithmic phase MRSA ~4×107 CFU diluted in cytodex bead-DPBS solution were injected subcutaneously into the right flank of prepared animals. Where indicated, 250 µg EP67, sEP67 or an equivalent volume of DPBS (50 µL) were injected sub-cutaneously into the right flank 24 h and 4 h prior to and 24 h following bacterial infection. Lesion size was measured on subsequent days using digital calipers. Ulcerative lesions were measured over time, harvested and homogenized using sterile 1 mm ceramic beads. Dilutions of the homogenate were placed on TS agar to enumerate bacterial colony forming units (cfu)

per g tissue. Mice (CD1) were rendered neutropenic as described previously (Hoesel L M, et al., Shock 2005; 24:40-47). Briefly, mice were injected intra-peritoneally with rat monoclonal anti-mouse Ly-6G antibody (RB6-8C5, eBioscience) or control rat immunoglobulin (IgG, eBioscience) 24 h prior to EP67 injection and subsequent bacterial infection as described above.

Measurement of cytokines. IL-6, TNF-α, INF-γ and KC inflammatory cytokines were measured in tissue homogenates as previously described using ELISA for IL-6, TNF-α, INF-γ (Morgan E L, et al., Vaccine;28:8275-8279), or according to manufacturer's protocols (BD and R&D Systems) for KC. Samples were run in triplicate.

Neutrophil chemotaxis and myeloperoxidase assay. Neutrophil recruitment at the site of injection by EP67 or sEP67 was examined using an in vivo chemotaxis assay as described previously (van Sorge N M, et al., PloS One 2008; 3:e2964). Briefly, 250 μg EP67 or sEP67 were injected subcutaneously into the right flank of CD1 mice. The injection was repeated after 24 h. Mice were euthanized 4 h after the second injection and the site of injection excised for histopathoglogic analysis or determination of myeloperoxidase (MPO) activity as described previously (van Sorge N M, et al., supra). The assay was carried out two times and the samples analyzed in duplicate.

Statistical analyses. Statistical analysis of results was analyzed by Student's t test using GraphPad Prism version 5. Significance was accepted at $P < 0.05$.

EP67 treatment reduces *S. aureus* cutaneous lesion formation in mice. In order to examine the effects of immunomodulatory peptide EP67 on CA-MRSA disease progression, a mouse model of ulcerative dermal infection was used (Bunce C, Infect Immun 1992; 60:2636-2640). Infection with CA-MRSA strain USA300 resulted in the formation of pus-filled lesions following sub-cutaneous injection with lesions reaching maximum diameter approximately 48-72 h post-infection. Prior to and post-MRSA infection, mice were injected with 250 μg EP67 or the scrambled peptide control, sEP67, as described in above. Disease progression was assessed via measurement of cutaneous lesion development. Lesion size was significantly reduced in animals treated with EP67 48 h post-bacterial inoculation, compared to the sEP67 Animals were sacrificed 5 days post-inoculation and lesion tissue excised and homogenized to determine bacterial CFU present within the lesions. A significant reduction in bacterial load was observed in MRSA-infected animals treated with EP67 compared to those treated with the sEP67 or PBS (data not shown) controls.

Proinflammatory cytokines are enhanced by EP67 treatment. The decrease in lesion size observed in EP67-treated animals indicated an enhanced immune activation in these animals. In order to determine the nature of the immune response activated by EP67 treatment, skin lesions were harvested 48 h post-infection and EP67 or sEP67 treatment, and subjected to ELISA to measure proinflammatory cytokines in tissue homogenates. Significantly higher levels of murine KC (homologue of human chemokine CXCL1) and IL-6 were observed in mice treated with EP67 compared to sEP67. EP67 treatment similarly resulted in an increase of TNF-α and INF-γ production during MRSA infection.

Neutrophil influx is essential for the protective action of EP67. Histopathologic analysis of skin tissue from representative mice revealed normal pathology following injection of PBS or sEP67, but massive influx of inflammatory cells, including neutrophils, following EP67 injection. Neutrophil recruitment to the site of EP67 injection was further analyzed using an in vivo neutrophil recruitment assay as described previously (van Sorge N M, et al., supra; and Banerjee A, et al., Cell Microbiol; 12:1576-1588). Neutrophil migration was assessed in skin homogenates following injection of EP67 or sEP67 by determining the level of neutrophil enzyme myeloperoxidase (MPO), which serves as an effective indication of neutrophil infiltration (Banerjee A, et al., supra; and Bradley P P, et al., J Invest Dermatol 1982; 78:206-209). This method compares well with other in vivo assays of neutrophil chemotaxis (van Sorge N M, et al., supra). MPO levels and therefore the number of accumulating neutrophils were significantly higher after injection with EP67 compared to the sEP67 control.

To further investigate the role of neutrophils in EP67-mediated MRSA lesion reduction, rat monoclonal antibody (Mab) RB6-8C5 was used to induce neutrophil depletion in CD-1 mice 24 h prior to MRSA infection and EP67 treatment. The dose of RB6-8C5 used in this study (25 μg) induced sustained level of neutropenia up to 72 h after injection of the antibody without affecting the population of Ly6G+ dendritic cells or other cell types (Daley J M, et al., J Leukoc Biol 2008; 83:64-70; Stephens-Romero S D, et al., Infect Immun 2005; 73:114-125; and Tvinnereim A R, et al., J Immunol 2004; 173:1994-2002). Consistent with the previous results, there was a significant reduction in lesion size in EP67-treated animals compared to sEP67-treated animals in the groups treated with the isotype IgG control antibody. However, there was no quantifiable difference in lesion size between animals treated with EP67 and sEP67 and with the RB6-8C5 Mab. In addition, both groups of neutopenic mice developed significantly larger lesions (P<0.001) than their respective IgG-treated paired control animals. These results indicate that neutrophil infiltration to the site of MRSA infection is essential for the reduction in lesion size mediated by EP67 treatment.

EP67 acts via the C5a receptor CD88. EP67 is a conformationally-biased analogue of the C-terminal region of human C5a (Morgan E L, et al., Vaccine 2009; 28:463-469). To examine whether EP67 reduces MRSA infection through a direct interaction with the C5a receptor, CD88, to induce a protective innate immune response, a CD88 −/− homozygous C57B1/6 line, CD88−/− and C57B1/6 CD88 +/+ controls were infected with MRSA sub-cutaneously and treated with EP67 or sEP67 as described in Materials and Methods. As seen previously in CD1 mice, wild-type CD88 +/+ animals treated with EP67 had significantly smaller lesions compared to those treated with sEP67. However, there was no difference in lesion size between the two treatment groups in CD88 −/− animals, indicating that EP67-mediated protection occurs via binding to CD88. EP67 and sEP67 treated groups in the CD88 −/− background developed lesions that were significantly larger than those treated with EP67 in the CD88 +/+background.

Sub-cutaneous injection of EP67 resulted in increased production of pro-inflammatory cytokines TNF-α, INF-γ, IL-6, as well as the neutrophil chemoattractant KC, in skin homogenates during active bacterial infection. Also, EP67 alone, even in the absence of bacteria, promoted the influx of inflammatory infiltrate that included neutrophils, as evidenced by increased levels of MPO and the visual presence of polymorphonuclear cells (PMNs) in skin tissue. The results also clearly show that neutrophil influx contributes to the EP67-mediated defense as depletion of this cell population abrogates the therapeutic effect of EP67.

EXAMPLE 3

Direct Killing of Bacteria by a C-terminal Analog of C5a

The following example demonstrates that a C-terminal analogue of C5a known as EP67 (YSFKDMP(MeL)aR (SEQ ID NO: 4)) induces killing of bacteria directly via a acteriostatic/bacteriocidal mechanism.

*E. coli* strain DH5α was grown overnight in mls of Lennox Broth (LB). This culture was diluted to an optical density at 60 nm ($OD_{600}$) of 0.06. The diluted *E.coli* was dispensed in 1.5 ml aliquots into separate tubes and 1.5 ml of EP67 (YSFKDMP(MeL)aR (SEQ ID NO: 4)), EP54 (YSFKPMPLaR (SEQ ID NO: 3)), scrambled-EP67 (s-EP67) or scrambled-EP54 in LB was added to obtain a final concentration of 500 µg/ml with the *E. coli* at an $OD_{600}$ of 0.03. A culture in LB was also prepared. The cultures were incubated at 37° C. with shaking and the $OD_{600}$ readings recorded hourly. In order to determine whether the growth media altered the effectiveness of EP67, LB was replaced with an alternative growth media, Tryptic Soy Broth (TSB).

Results demonstrated that EP67 induces direct bacteriostatic/bacteriocidal effects in the absence of any antigen presenting cells or immune effector cells and that this direct effect is independent of the varying composition of the media the bacteria are grown in.

To test the efficacy of EP67 on bacteria growing in log phase, overnight cultures of DH5α were grown in either LB or TSB. The cultures were diluted to an $OD_{600}$ of 0.03 and incubated at 37° C. with shaking until they reached an $OD_{600}$ of 0.2 at which time either EP67 or s-EP67, in the appropriate media, were added to a final concentration of 500 µg/m. DH5α control cultures (absence of additives) were also prepared. The tubes were further shaken at 37° C. and $OD_{600}$ readings were taken hourly.

The results were consistent with the discussed above; EP67 was shown to significantly reduce and/or stop log phase growth, while s-EP67 demonstrated little or no effect on growth.

*S. aureus* In Vitro EP67 Killing Curves

150 µl of LB growth medium plus 50 µl of EP67 or s-EP67 were added to individual culture wells resulting in a dilution series of 6 wells per EP67 or s-EP67. A "no EP67" well (control) was included at the end of each series. *S. aureus* (Newman strain) was allowed to grow to an $OD_{600}$ of 0.4 and each well of the dilution series was inoculated with 5µl of the culture. Two wells with no bacterial inoculums were included to serve as controls. Plates were incubated at 37° C. with agitation and the $OD_{600}$ of each well was measured hourly using a plate reader.

The results showed a dose dependent inhibitory effect of EP67 on bacterial growth at higher concentrations used in the experiment.

EXAMPLE 4

Effect of a C-terminal Analog of C5a on Group B *Streptococcus* (GBS) Meningitis In this study, EP67 was used to demonstrate the ability to induce host innate immune responses that are protective to a bacterial infection common in the central nervous system (CNS) via administration at a site distal to the CNS.

8-week old female CD1 mice were treated with 250 ug of EP67 or s-EP67 at day −1, 0, 1 and 2 via i.p. injection. GBS was injected via i.p. at $1\times10^9$ cfu/mouse. Brains and blood were harvested from each mouse 96 hours post-injection. The tissue was homogenized, diluted and plated to determine the cfu/g bacteria.

The results demonstrated that EP67 induces a robust host innate immune response that protects against GBS infections in the central nervous system. These results indicate that EP67 (and related analogues) can be used to invoke protective innate immunity in immune-privileged sites and further support its use as an immunotherapeutic for systemic pathogenic infections.

EXAMPLE 5

Effect of a C-terminal Analog of C5a on Bacterial Burden of a Biofilm

In this study, EP67 was used to demonstrate the ability to induce host innate immune responses capable of eliminating/reducing bacterial burden of a biofilm associated with a catheter.

A *S. aureus* (USA300 LAC strain) biofilm was established on a hollow catheter (1 cm in length) inserted subcutaneously into C57BL/6 mice by introducing 1000 CFUs of *S. aureus* into the catheter lumen. At the time of infection, one dose of EP67 (200 µg/ml dissolved in PBS) was introduced. At both 24 and 48 h following infection, a series of four injections of EP67 were made; two into each open end of the catheter (20 µl each) and two along the top and bottom at points perpendicular to the middle of the catheter (50 µl each). Samples of the biofilm and surrounding tissue were obtained at Day 3 and assessed for the presence of viable bacteria by standard culture methods. Mice treated with EP67 exhibited a significant decrease in bacterial burdens within the biofilm and surrounding tissue relative to mice treated with the inactive, scrambled EP67 (sEP67) and PBS vehicle.

The invention claimed is:

1. A method of activating an immune cell at a site of infection or disease comprising administering an effective amount of an oligopeptide C-terminal analog of C5a to a mammal, wherein said immune cell is an antigen presenting cell, said analog not attached to an antigen, and said analog having response-selective C5a receptor binding activity, wherein the analog is SEQ ID NO: 4.

2. The method according to claim 1, wherein the analog is administered by a route selected from the group consisting of oral, topical, inhalation spray, intradermal, subcutaneous injection, and intravenous injection.

3. The method according to claim 1, wherein the analog is formulated in a powder, aerosol, cream, gel, liquid, bandage, and surgical suture.

4. The method according to claim 1, wherein the analog is administered at a dose of 25 μg to 500 μg.

5. The method according to claim 1, wherein the analog is administered concurrently, prior, or following administration of a second therapeutic agent.

6. The method according to claim 5, wherein the second therapeutic agent is selected from the group consisting of immunosuppressants, vaccines, corticosteroids, anti-inflammatory agents, chemotherapeutic agents, antibiotics, antifungals, antivirals, and antiparasitics.

7. The method according to claim 6, wherein the vaccine is a C-terminal analog of C5a attached to an antigen.

8. The method according to claim 1, comprising administering a composition comprising a therapeutically effective amount of the analog and a pharmaceutically acceptable carrier.

9. The method according to claim 1, wherein the analog is administered as a dosage unit form.

\* \* \* \* \*